(12) United States Patent
Chen et al.

(10) Patent No.: US 11,661,421 B2
(45) Date of Patent: May 30, 2023

(54) INDOLIZINE COMPOUNDS, PREPARATION METHOD AND USE THEREOF

(71) Applicant: HAIHE BIOPHARMA CO., LTD., Shanghai (CN)

(72) Inventors: Xuxing Chen, Shanghai (CN); Yi Chen, Shanghai (CN); Ying Huang, Shanghai (CN); Meiyu Geng, Shanghai (CN); Qiong Zhang, Shanghai (CN); Jian Ding, Shanghai (CN); Yucai Yao, Shanghai (CN); Qianqian Shen, Shanghai (CN); Yanyan Shen, Shanghai (CN)

(73) Assignee: HAIHE BIOPHARMA CO., LTD., Shanghai (CN)

( * ) Notice: Subject to any disclaimer, the term of this patent is extended or adjusted under 35 U.S.C. 154(b) by 204 days.

(21) Appl. No.: 16/978,501

(22) PCT Filed: Mar. 5, 2019

(86) PCT No.: PCT/CN2019/076904
§ 371 (c)(1),
(2) Date: Sep. 4, 2020

(87) PCT Pub. No.: WO2019/170063
PCT Pub. Date: Sep. 12, 2019

(65) Prior Publication Data
US 2020/0399270 A1   Dec. 24, 2020

(30) Foreign Application Priority Data
Mar. 6, 2018 (CN) .......................... 201810183618.4

(51) Int. Cl.
*C07D 471/04* (2006.01)
(52) U.S. Cl.
CPC ................. *C07D 471/04* (2013.01)
(58) Field of Classification Search
CPC .................................................. C07D 471/04
See application file for complete search history.

(56) References Cited

FOREIGN PATENT DOCUMENTS

| CN | 102970869 A | 3/2013 |
| CN | 103987842 A | 8/2014 |
| WO | 2016102493 A1 | 6/2016 |
| WO | 2018045971 A1 | 3/2018 |

OTHER PUBLICATIONS

Pinedo et al. (2000) McMahon et al. (2000).*
Wolff et al. (1997).*
Banker (1996).*
Vippagunta et al. (2001).*
International Search Report issued in corresponding PCT Application No. PCT/CN2019/076904 dated May 30, 2019.

* cited by examiner

*Primary Examiner* — Paul V Ward
(74) *Attorney, Agent, or Firm* — Carter, DeLuca & Farrell LLP

(57) ABSTRACT

The invention provides an indolizine compound represented by formula I or a pharmaceutically acceptable salt thereof, a preparation method and a use thereof. The indolizine compound has an inhibitory effect on wild-type and/or mutant EZH2 or EZH1, and is expected to be developed into a novel drug for anti-tumor or for the treatment of autoimmune diseases.

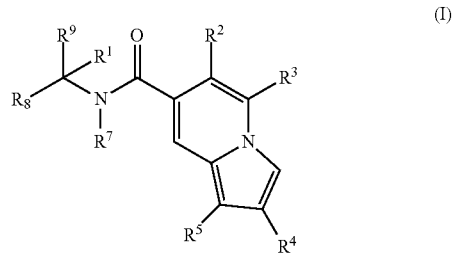

9 Claims, No Drawings

INDOLIZINE COMPOUNDS, PREPARATION METHOD AND USE THEREOF

CROSS REFERENCE TO RELATED APPLICATIONS

This application is a national stage application of International Application No. PCT/CN2019/076904, filed Mar. 5, 2019, which claims the benefit of and priority to Chinese Patent Application No. 201810183618.4, filed Mar. 6, 2018, the entire contents of each of which are hereby incorporated by reference herein in their entirety.

TECHNICAL FIELD

The present invention pertains to the field of medicinal chemistry, in particular, the present invention relates to an indolizine compound or pharmaceutically acceptable salts and a preparation method thereof. The indolizine compounds according to the present invention can be used for preparing a medicament for the treatment of diseases associated with the Enhancer of Zeste homolog 1/2 (EZH1/2) (*Drosophila*), such as malignant tumors.

BACKGROUND

Epigenetic refers to that the nucleotide sequence of a gene does not change, but the gene expression has undergone a heritable change. This phenomenon plays an important role in regulating processes including proliferation, differentiation, survival and apoptosis of cells. An important mechanism of epigenetic regulation is histone covalent modification. In eukaryotic cells, DNA winds around histones to form a nucleosome, which is the basic structure of chromatin. In each nucleosome, a histone octamer is formed by 2 molecules each of H2A, H2B, H3 and H4. A variety of covalent modifications will occur at the N-terminal amino acid end of each histone, such as methylation, acetylation, phosphorylation, ubiquitination, etc., to control gene expression. Enzymes that catalyze histone methylation are referred as histone methyltransferases (HMTs).

Polycomb repressive complex 2, namely PRC2, is a multi-protein complex that has the function of catalyzing the methylation of histone H3 at lysine 27 (H3K27), thus silencing related genes. The catalytic subunit of PRC2 is EZH1 or EZH2. EZH1 or EZH2 alone has no catalytic function, and they can play the role of transmethylation only if they bind to EED (embryonic ectoderm development) and SUZ12 (suppressor of zeste 12 homolog). EZH2 is highly expressed in cells of various tumors (such as breast cancer, colorectal cancer, endometrial tumor, gastric cancer, liver cancer, renal cancer, lung cancer, melanoma, ovarian cancer, pancreatic cancer, prostate cancer and bladder cancer, etc.), which is closely related to the proliferation, invasion, drug resistance and migration processes of tumor cells.

In recent years, it have been found that 8-24% of non-Hodgkin's lymphomas involves EZH2 mutations, such as Y641F, Y641N, Y641S, Y641H, A677G, and A687V, etc. Compared with wild-type EZH2, these mutants have enhanced catalytic activity in dimethylation and trimethylation of histone H3 at lysine 27. Both of overexpression and mutation of EZH2 can cause an increased level of H3 lysine 27 trimethylation product (H3K27me3). A high level of H3K27me3 plays an important role in the proliferation and survival of tumor cells. Abnormal activity of EZH2 leads to the occurrence and development of tumors, and it may be one of the important mechanisms that the multiple target genes for regulating EZH2 are tumor suppressor genes and tumor suppressor genes are silenced. Down-regulation of EZH2 by siRNA or shRNA or indirect inhibition of EZH2 by the SAH hydrolase inhibitor, 3-deazaneplanocin A (3-DZNep) can significantly reduce tumor cell proliferation and invasion in vitro and tumor growth in vivo.

EZH2 also plays an important role in the differentiation of T cells. EZH2 reduces the expression of Th1/Th2 cytokines, such as IFN-γ, IL-4, IL-5, etc., inhibits Th1/Th2-dependent T cell migration, and activates regulatory T cells. In the tumor microenvironment, it is an important mechanism for tumor immune escape that EZH2 inhibits the secretion of chemokines such as CXCL9 and CXCL10 in Th1 cells.

Therefore, it is highly urgent in the field to develop drugs that are effective in inhibiting wild-type and/or mutant EZH1/2.

SUMMARY OF THE INVENTION

It is one object of the present invention to provide an indolizine compound or a pharmaceutically acceptable salt thereof.

It is another object of the present invention to provide a method for preparing the indolizine compound or the pharmaceutically acceptable salt thereof.

It is still another object of the present invention to provide a pharmaceutical composition containing the indolizine compound or the pharmaceutically acceptable salt thereof.

It is yet another object of the present invention to provide a use of the indolizine compound or the pharmaceutically acceptable salt thereof or the composition containing the indolizine compound or the pharmaceutically acceptable salt thereof in the preparation of a medicine for anti-tumor, or for prevention and/or treatment of autoimmune diseases.

In the first aspect, the present invention provides an indolizine compound represented by formula I, a pharmaceutically acceptable salt, an enantiomer, a diastereomer, a tautomer, a solvate, a polymorph or a prodrug thereof,

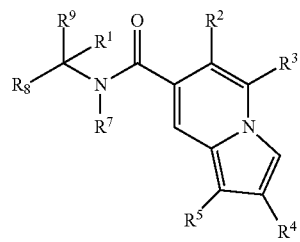

I

Wherein,
$R^1$ is selected from the group consisting of

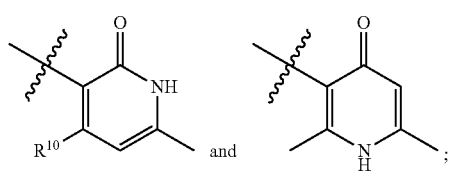

$R^{10}$ is selected from the group consisting of H, halogen, —$NH_2$, —$NO_2$, optionally substituted C1-C6 alkyl and optionally substituted C1-C4 alkoxy;

R[2] is selected from the group consisting of H, halogen, cyano and optionally substituted C1-C6 alkyl;

R[3] is

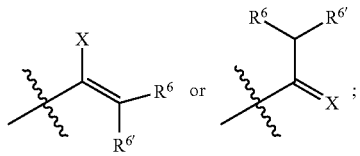

R[6] and R[6'] are each independently selected from the group consisting of H, methyl, ethyl, propyl and cyclopropyl, and at least one of R[6] and R[6'] is H;

X is an optionally substituted saturated or unsaturated 4-7 membered cyclic hydrocarbyl group or an optionally substituted 4-7 membered saturated or unsaturated heterocyclic group, and the heterocyclic group contains 1-2 heteroatoms selected from O, N, S, P;

R[4] and R[5] are independently selected from the group consisting of H, halogen, —COOH, —CN, optionally substituted C1-C6 alkyl, optionally substituted 6-16 membered aryl, optionally substituted 5-16 membered heteroaryl, optionally substituted 4-8 membered saturated or unsaturated cycloalkyl, optionally substituted 4-8 membered saturated or unsaturated heterocyclic group, optionally substituted C1-C6 alkylcarbonyl, optionally substituted —C(O)O—(C1-C6 alkyl), —C(O)(NR[a]R[b]), dihydroxyboryl, optionally substituted C2-C8 alkenyl, optionally substituted C2-C8 alkynyl, optionally substituted C1-C6 alkyl sulfonyl group, optionally substituted C1-C6 alkyl sulfoxide group and optionally substituted C1-C6 alkyl mercapto group; wherein, the heteroaryl or heterocyclic group contains 1-3 heteroatoms selected from N, O, S, P; wherein, R[a] and R[b] are each independently selected from the group consisting of H, optionally substituted C1-C6 alkyl, optionally substituted 3-8 membered cycloalkyl, and optionally substituted 4-8 membered heterocyclic group, or R[a] and R[b] are connected together with N to form an optionally substituted 4-8 membered heterocyclic ring; wherein the heterocyclic ring contains 1-3 heteroatoms selected from N, O, S, P;

R[7] is selected from the group consisting of H and optionally substituted C1-C6 alkyl;

R[8] and R[9] are each independently selected from the group consisting of hydrogen, deuterium and optionally substituted C1-C6 alkyl;

The optionally substituted substituents in R[2], R[7], R[1], R[9], R[10], R[a] and R[b] include one or more (e.g., 1, 2, 3 or 4) substituents selected from the group consisting of H, halogen, C1-C4 alkyl, C1-C4 haloalkyl, nitro, —OH, amino, methoxy, dimethylamino.

In another preferred embodiment,

R[1] is

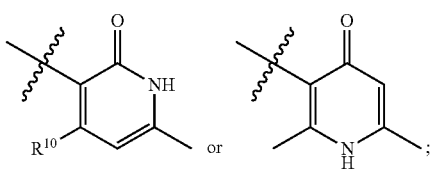

R[10] is selected from the group consisting of H, halogen, —NH₂, —NO₂, optionally substituted C1-C6 alkyl and optionally substituted C1-C4 alkoxy;

R[2] is selected from the group consisting of H, halogen, cyano and optionally substituted C1-C6 alkyl;

R[3] is

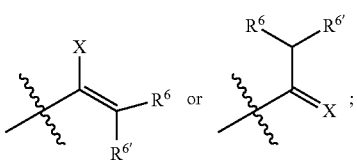

R[6] and R[6'] are each independently selected from the group consisting of H, methyl, ethyl, propyl and cyclopropyl, and at least one of R[6] and R[6'] is H;

X is selected from the group consisting of an optionally substituted saturated or unsaturated 4-7 membered cyclic hydrocarbyl group, or an optionally substituted 4-7 membered saturated or unsaturated heterocyclic group; wherein, the heterocyclic group contains 1-2 heteroatoms selected from O, N, S, P; the substituent in X is selected from the group consisting of —OH, halogen, tert-butyloxycarbonyl (Boc), —NR[s]R[t], C1-C4 alkyl substituted with 1-3 R[x]s, C1-C4 alkoxy substituted with 1-3 R[x]s, C1-C4 alkylcarbonyl substituted with 1-3 R[x]s, C1-C4 alkoxycarbonyl substituted with 1-3 R[x]s and C1-C4 alkylsulfonyl substituted with 1-3 R[x]s; each R[x] is independently selected from the group consisting of H, halogen, methylamino, dimethylamino, amino, —OH, methoxy and ethoxy;

R[s] and R[t] are each independently selected from the group consisting of: H, C1-C4 alkyl, C1-C4 haloalkyl,

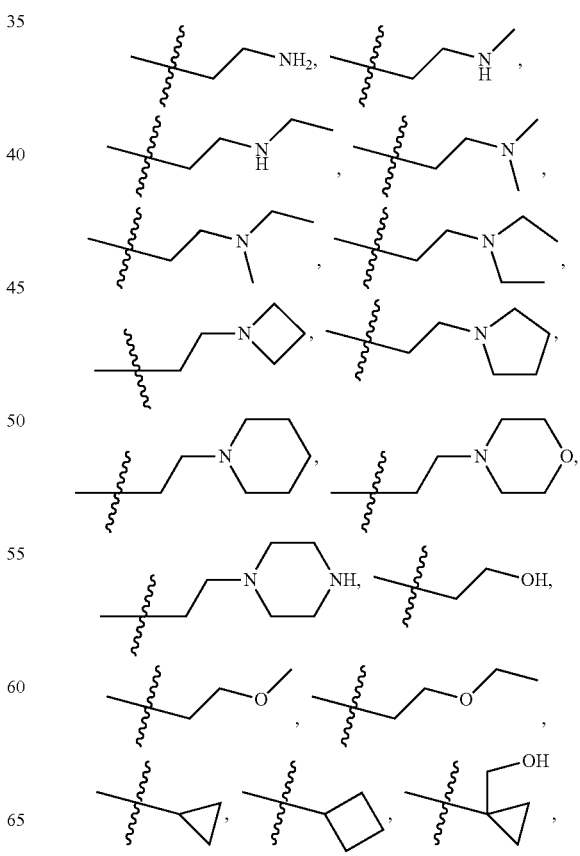

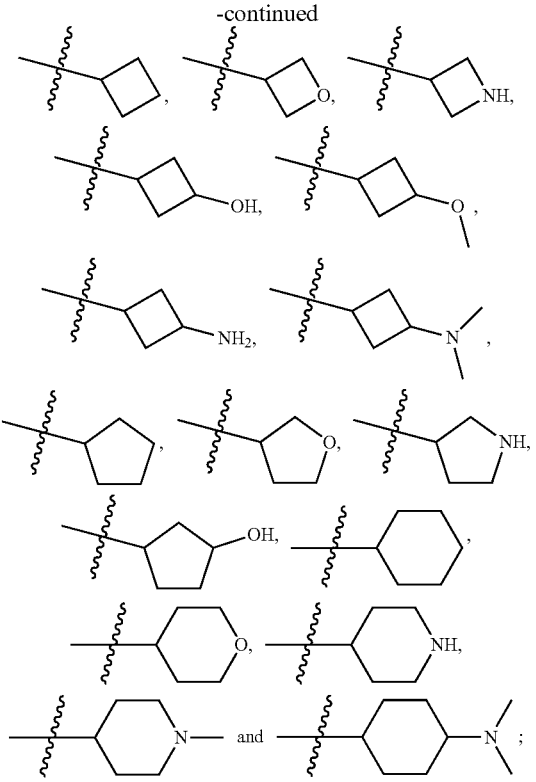

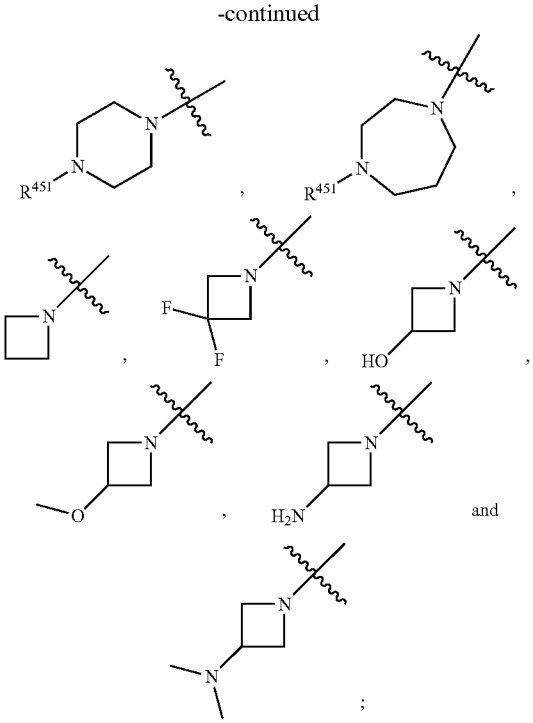

R⁴ and R⁵ are each independently selected from the group consisting of H, halogen, —COOH, —CN, optionally substituted C1-C6 alkyl, optionally substituted 6-16 membered aryl, optionally substituted 5-16 membered heteroaryl, optionally substituted 4-8 membered saturated or unsaturated cycloalkyl, optionally substituted 4-8 membered saturated or unsaturated heterocyclic group, optionally substituted C1-C6 alkylcarbonyl, optionally substituted —C(O)O—(C1-C6 alkyl), —C(O)(NR$^a$R$^b$), dihydroxyboryl, optionally substituted C2-C8 alkenyl, optionally substituted C2-C8 alkynyl, optionally substituted C1-C6 alkyl sulfonyl group, optionally substituted C1-C6 alkyl sulfoxide group and optionally substituted C1-C6 alkyl mercapto group; the heteroaryl or heterocyclic group contains 1-3 heteroatoms selected from N, O, S, P; and the substituents in R⁴ and R⁵ are selected from the group consisting of halogen, —CN, R⁴⁵ (C1-C4 alkyl), R⁴⁵ (C1-C4 alkoxy), R⁴⁵ (C1-C4 alkyl) acyl, R⁴⁵ (C1-C4 alkyl) sulfonyl, R⁴⁵ (C3-C8 cycloalkyl), R⁴⁵ (4-8 membered heterocyclic group) and —NR$^c$R$^d$; the heterocyclic group is a heterocyclic group containing 1-2 heteroatoms selected from N and O;

Each R⁴⁵ is independently selected from the group consisting of H, —OH, halogen, -Boc, halogenated C1-C4 alkyl, C1-C4 alkyl, C1-C4 alkoxy, C1-C4 acyl, dimethylamino, methylamino, diethylamino, methylethylamino, ethylamino,

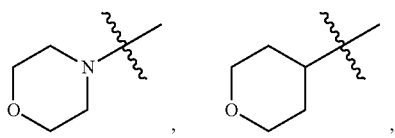

and R⁴⁵¹ is selected from the group consisting of H, C1-C4 alkyl; wherein, R$^a$ and R$^b$ are each independently selected from H, optionally substituted C1-C6 alkyl, optionally substituted 3-8 membered cycloalkyl and optionally substituted 4-8 membered heterocyclic group, or R$^a$ and R$^b$ are connected together with N to form optionally substituted 4-8 membered heterocyclic ring; wherein the heterocyclic ring contains 1-3 heteroatoms selected from N, O, S and P;

R$^c$ and R$^d$ are each independently selected from the group consisting of: H, C1-C4 alkyl, C1-C4 haloalkyl

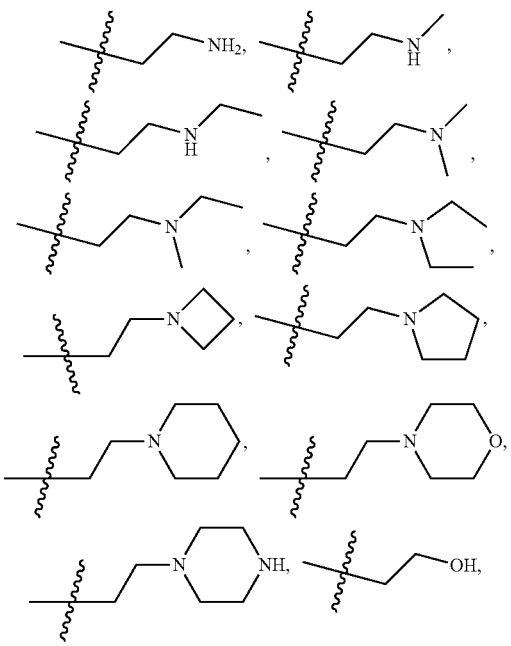

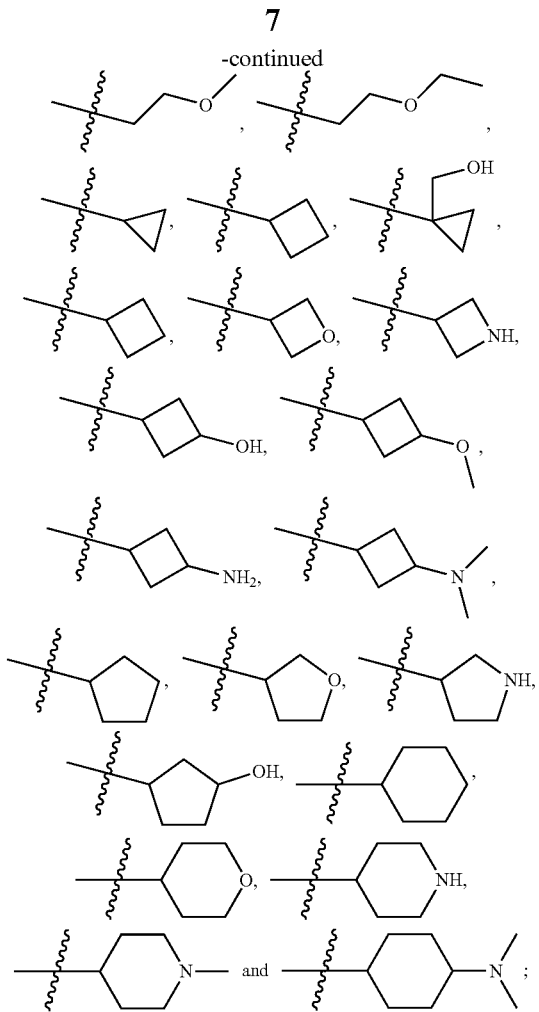

R[7] is selected from the group consisting of H and optionally substituted C1-C6 alkyl;

R[8] and R[9] are each independently selected from the group consisting of hydrogen, deuterium and optionally substituted C1-C6 alkyl;

The substituted substituents in R[2], R[7], R[8], R[9], R[10], R[a], and R[b] include one or more (e.g., 1, 2, 3, or 4) substituents selected from the group consisting of H, halogen, C1-C4 alkyl, C1-C4 haloalkyl, nitro, —OH, amino, methoxy and dimethylamino.

In another preferred embodiment, R[2] is optionally substituted C1-C4 alkyl; preferably methyl.

In another preferred embodiment, R[3] is selected from the group consisting of:

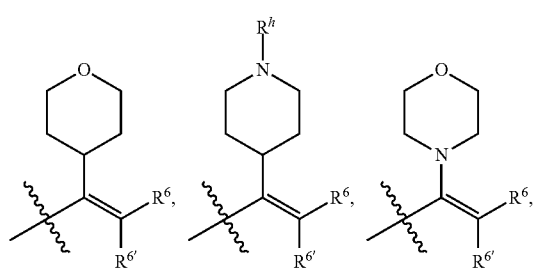

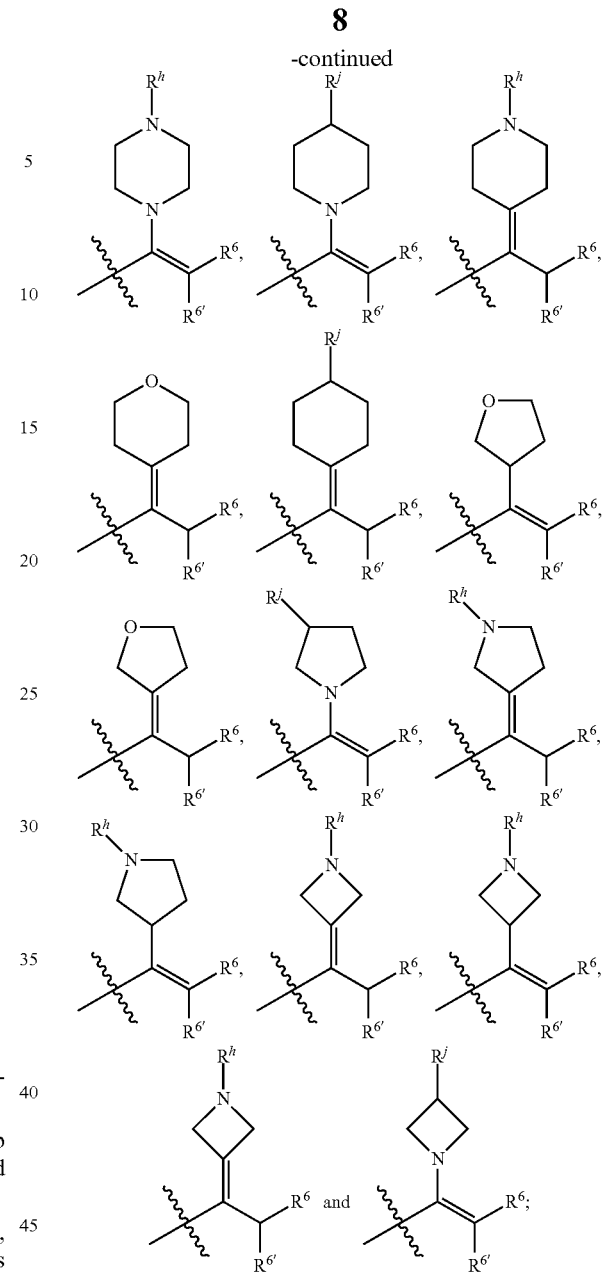

Wherein R[h] is selected from the group consisting of H, C1-C4 alkyl substituted with 1-3 R[x]s, C1-C4 alkylcarbonyl substituted with 1-3 R[x]s, C1-C4 alkoxycarbonyl substituted with 1-3 R[x]s, C1-C4 alkylsulfonyl substituted with 1-3 R[x]s and Boc;

R[j] is selected from the group consisting of —OH, halogen, C1-C4 alkyl substituted with 1-3 R[x]s, C1-C4 alkoxy substituted with 1-3 R[x]s, and —NR[s]R[t];

R[x] is selected from the group consisting of H, halogen and —OH;

R[s] and R[t] are each independently selected from the group consisting of H, C1-C4 alkyl, C1-C4 haloalkyl,

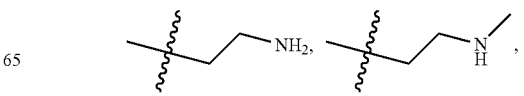

-continued
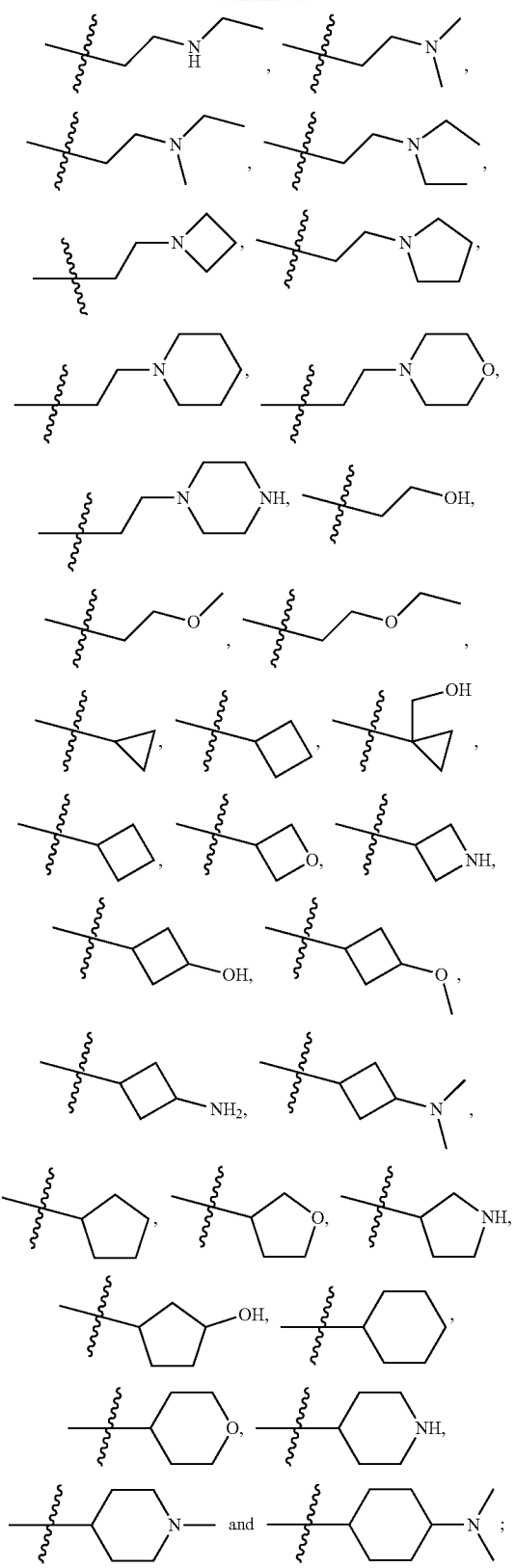
$R^6$ and $R^{6'}$ are each independently selected from the group consisting of H, methyl and ethyl, and at least one of $R^6$ and $R^{6'}$ is H;
Preferably, $R^3$ is selected from the group consisting of:
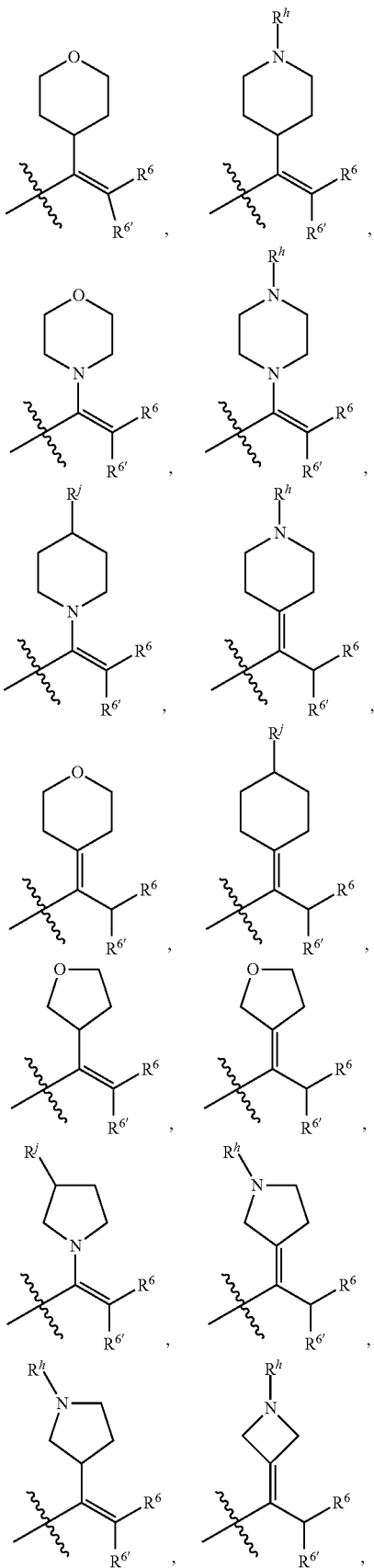

-continued

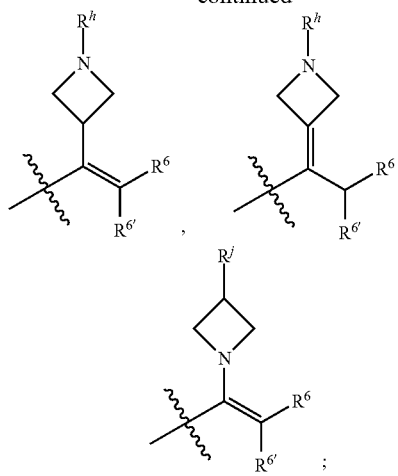

Wherein R^h is selected from the group consisting of H and R^x (C1-C3 alkyl);
R^j is selected from the group consisting of —OH, halogen, R^x (C1-C3 alkyl), R^x (C1-C3 alkoxy) and —N(C1-C3 alkyl)$_2$;
R^x is selected from the group consisting of H, halogen, trifluoromethyl and difluoromethyl;
R^6 and R^6' are each independently selected from the group consisting of H, methyl and ethyl, and at least one of R^6 and R^6' is H;

Most preferably,
R^3 is selected from the group consisting of:

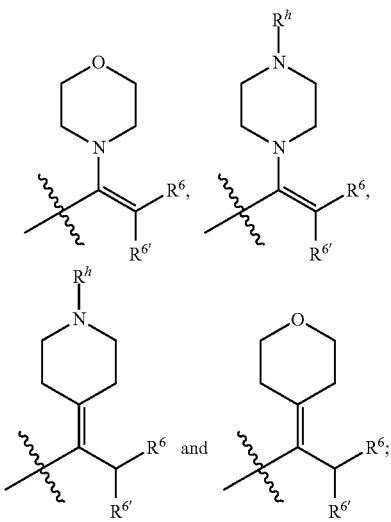

R^h is selected from C1-C3 alkyl substituted with fluorine;
R^6 and R^6' are each independently selected from H and methyl, and at least one of R^6 and R^6' is H.

In another preferred embodiment, R^4 and R^5 are each independently selected from the group consisting of: H, R^55 C1-C4 alkyl, —CN, halogen, R^55 C1-C4 alkylcarbonyl, R^55 (C1-C4 alkoxy) carbonyl, —COOH, —C(O)(NR^a R^b),

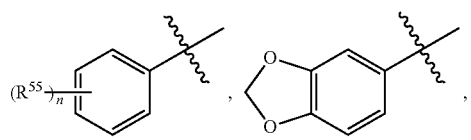

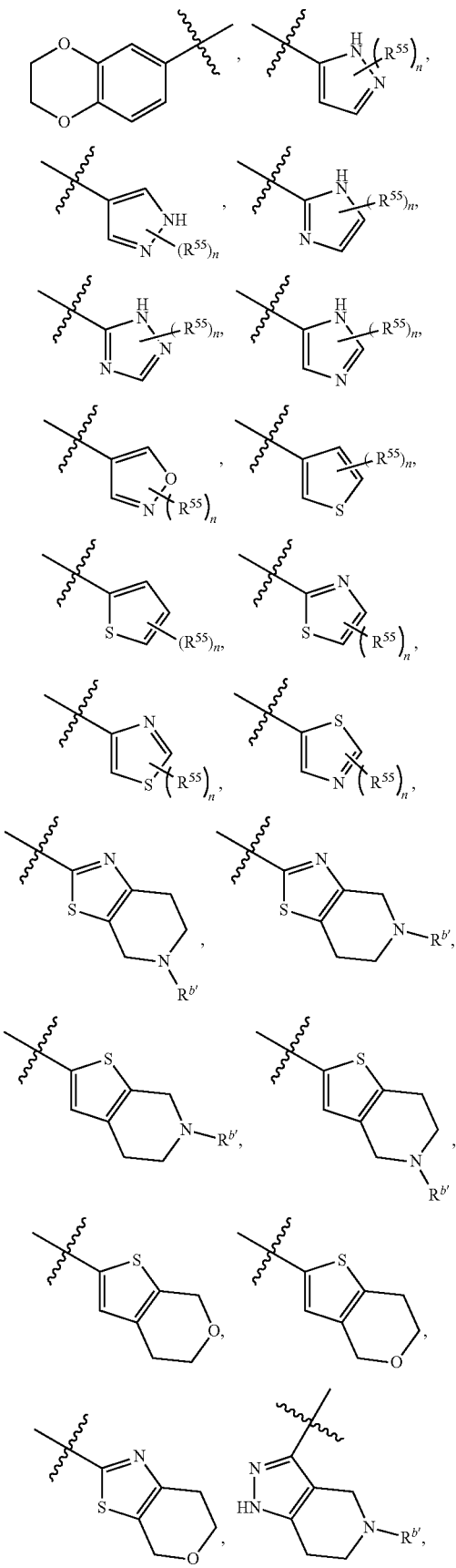

-continued

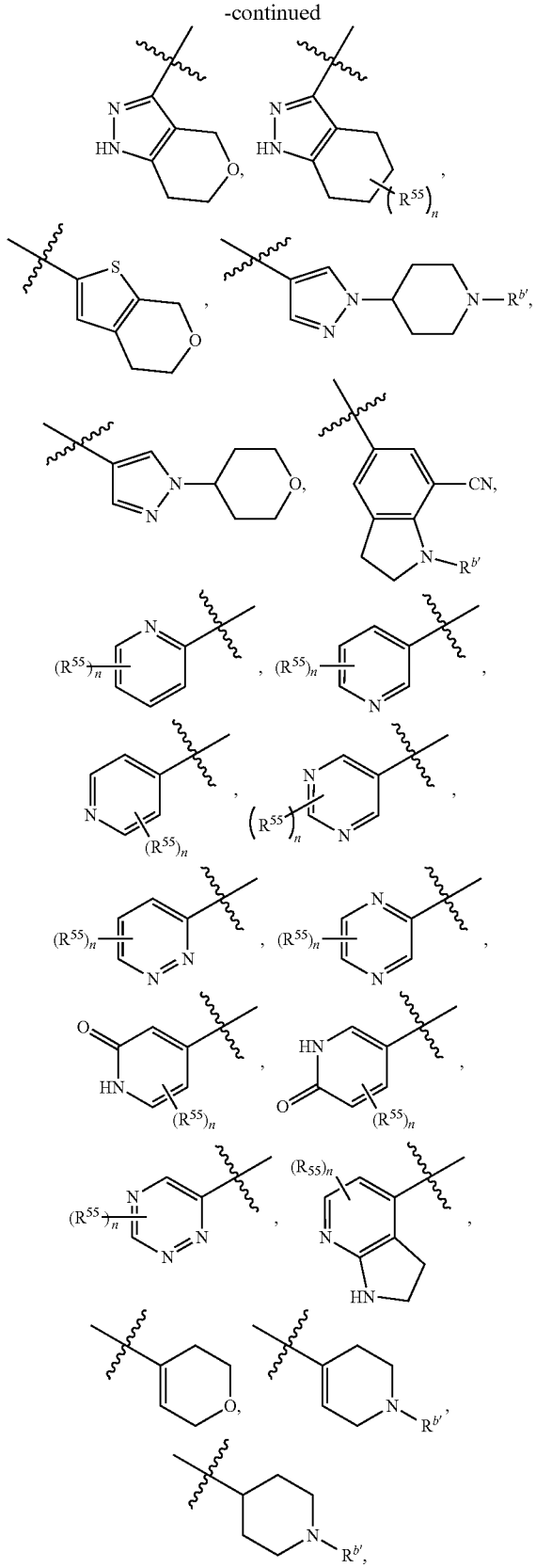

and $R^{55}$C1-C3 alkynyl;

n is the number of $R^{55}$ substituents, and is selected from 1, 2 and 3;

$R^{55}$ is selected from the group consisting of H, $R^{551}$C1-C4 alkyl, $R^{551}$C3-C8 cycloalkyl, halogen, —CN, —NR$^c$R$^d$, ($R^{551}$C1-C4 alkyl)O—, $R^{551}$C1-C4 alkyl sulfonyl group,

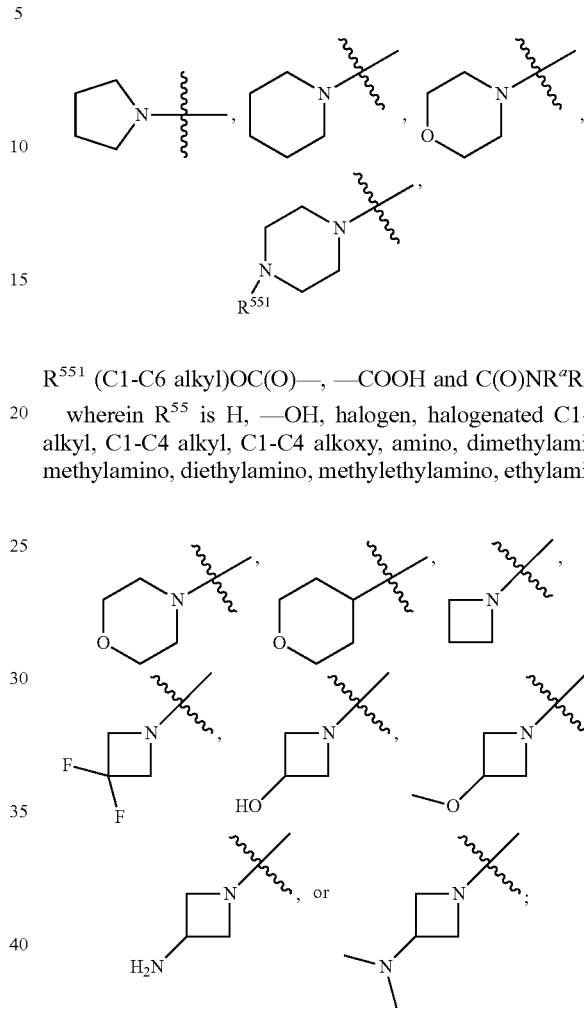

$R^{551}$ (C1-C6 alkyl)OC(O)—, —COOH and C(O)NR$^a$R$^b$);

wherein $R^{55}$ is H, —OH, halogen, halogenated C1-C4 alkyl, C1-C4 alkyl, C1-C4 alkoxy, amino, dimethylamino, methylamino, diethylamino, methylethylamino, ethylamino, $R^a$ and $R^b$ are each independently selected from the group consisting of H, C1-C4 alkyl, R$^{b''}$(C1-C4)alkyl, phenyl, halophenyl, and R$^{b'}$ substituted heterocyclic group; or $R^a$ and $R^b$ are connected together with N to form a 4-8 membered heterocyclic group substituted with R$^{b'}$, the heterocyclic group contains 1-2 heteroatoms selected from N and O;

R$^{b''}$ is selected from the group consisting of H, —OH, C1-C3 alkoxy, dimethylamino,

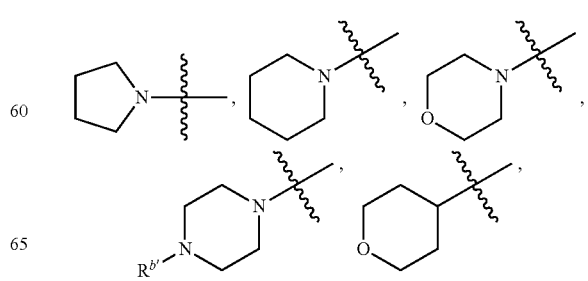

15

-continued

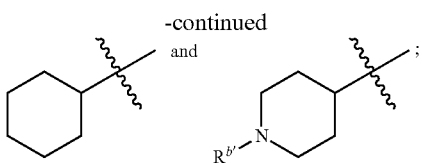
and $R^{b'}$ is selected from the group consisting of H, C1-C4 alkyl, Boc and C1-C4 acyl;

Preferably, $R^4$ and $R^5$ are each independently selected from the group consisting of H,

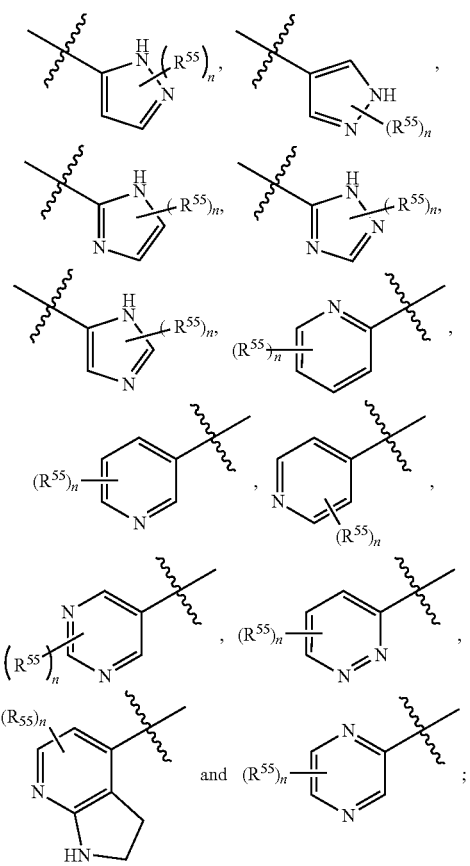

n is the number of $R^{55}$ substituents, and is selected from 1 and 2;

$R^{55}$ is selected from the group consisting of H, C1-C4 alkyl, halogen, $-NH_2$, (C1-C2 alkyl)NH— and dimethylamino.

In another preferred embodiment, $R^3$ is

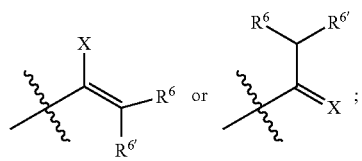

$R^6$ and $R^{6'}$ are each independently selected from the group consisting of H, methyl, ethyl and propyl, and at least one of $R^6$ and $R^{6'}$ is H;

16

X is selected from the group consisting of optionally substituted pyranyl, optionally substituted piperidinyl, optionally substituted piperazinyl and optionally substituted morpholinyl, and the substituent in X is selected from the group consisting of C1-C4 alkyl and halogenated C1-C4 alkyl; preferably, the substituent in X is trifluoroethyl;

$R^2$ is methyl;

$R^{10}$ is selected from the group consisting of unsubstituted or halogenated C1-C4 alkyl and unsubstituted or halogenated C1-C4 alkoxy;

$R^4$ and $R^5$ are each independently selected from the group consisting of H, optionally substituted pyridyl, optionally substituted pyrimidinyl, optionally substituted pyridazinyl, optionally substituted pyrazolyl, optionally substituted triazolyl and optionally substituted pyrrolopyridyl;

The substituents in $R^4$ and $R^5$ are selected from the group consisting of H, C1-C4 alkyl, halogen and $-NR^cR^d$;

$R^c$ and $R^d$ are each independently selected from the group consisting of H, C1-C4 alkyl and halogenated C1-C4 alkyl.

In another preferred embodiment, $R^2$ is methyl;

$R^3$ is

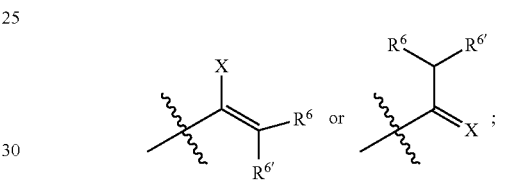

$R^6$ and $R^{6'}$ are each independently selected from H or methyl, and at least one of $R^6$ and $R^{6'}$ is H;

X is selected from the group consisting of morpholinyl, trifluoroethylpiperazinyl and trifluoroethylpiperidinyl; further preferably, morpholinyl, 2,2,2-trifluoroethylpiperazinyl or 2,2,2-trifluoroethyl piperidinyl;

$R^4$ and $R^5$ are each independently selected from the group consisting of H, dimethylaminopyridine and methylaminopyridine; further preferably, are each independently H, 2-dimethylaminopyridine or 2-methylaminopyridine;

$R^7$, $R^8$ and $R^9$ are hydrogen;

$R^{10}$ is methoxy.

In another preferred embodiment, the indolizine compound represented by Formula I is selected from the following compounds:

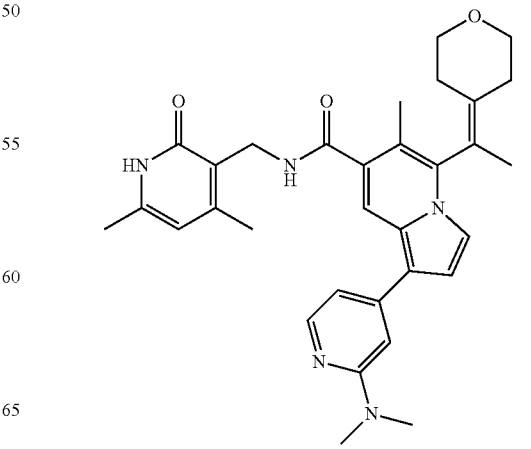

,

17 -continued
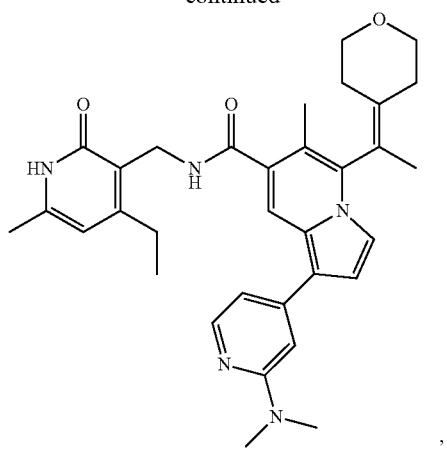
,
18 -continued
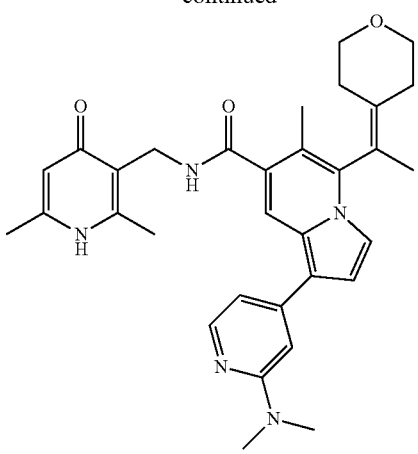
,
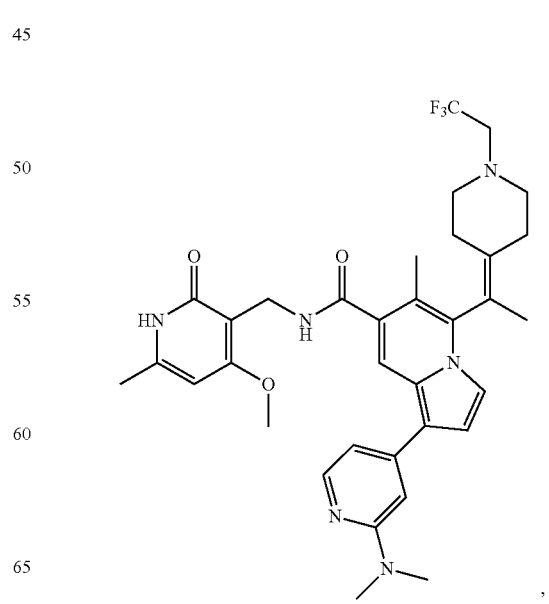
,

-continued
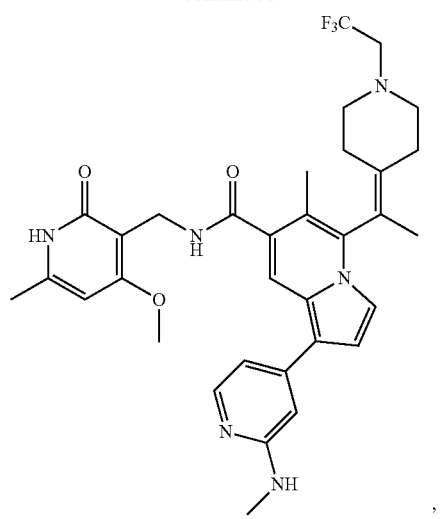
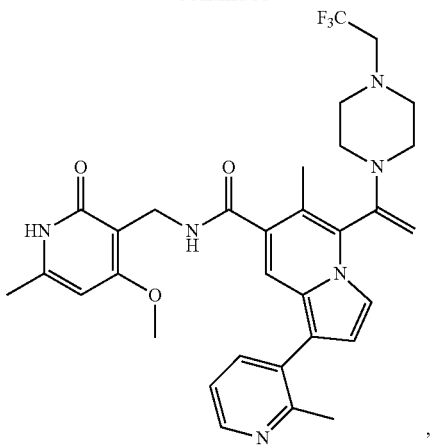
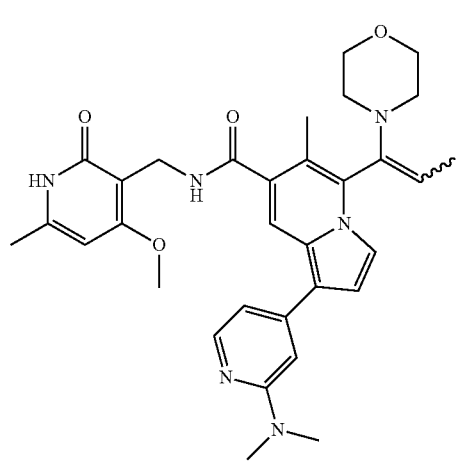
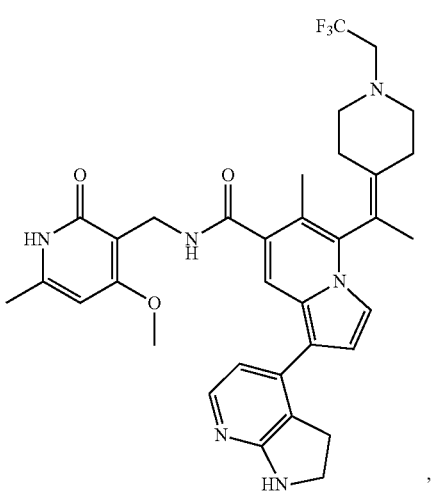
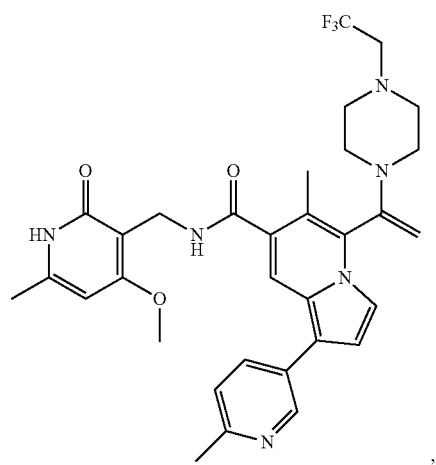
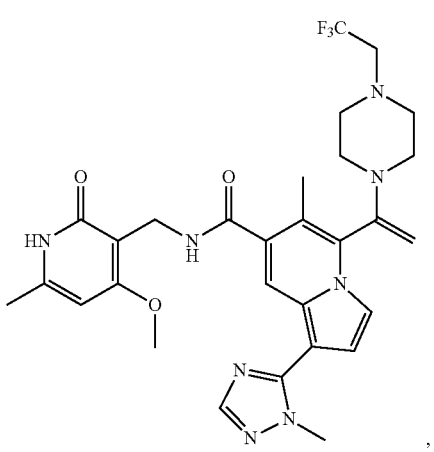

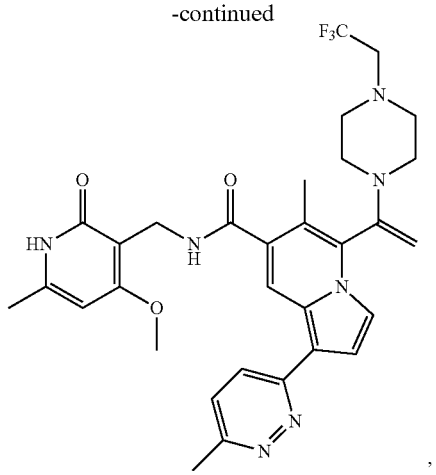
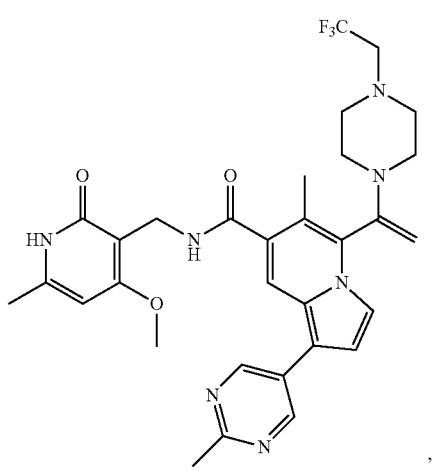
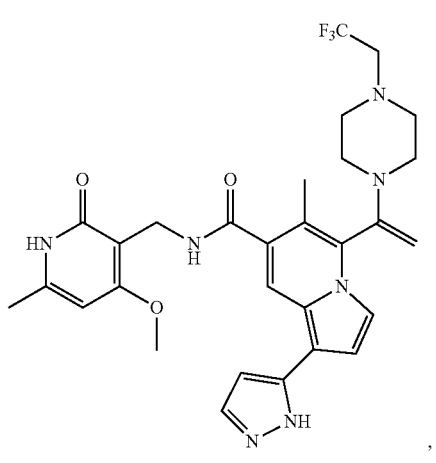
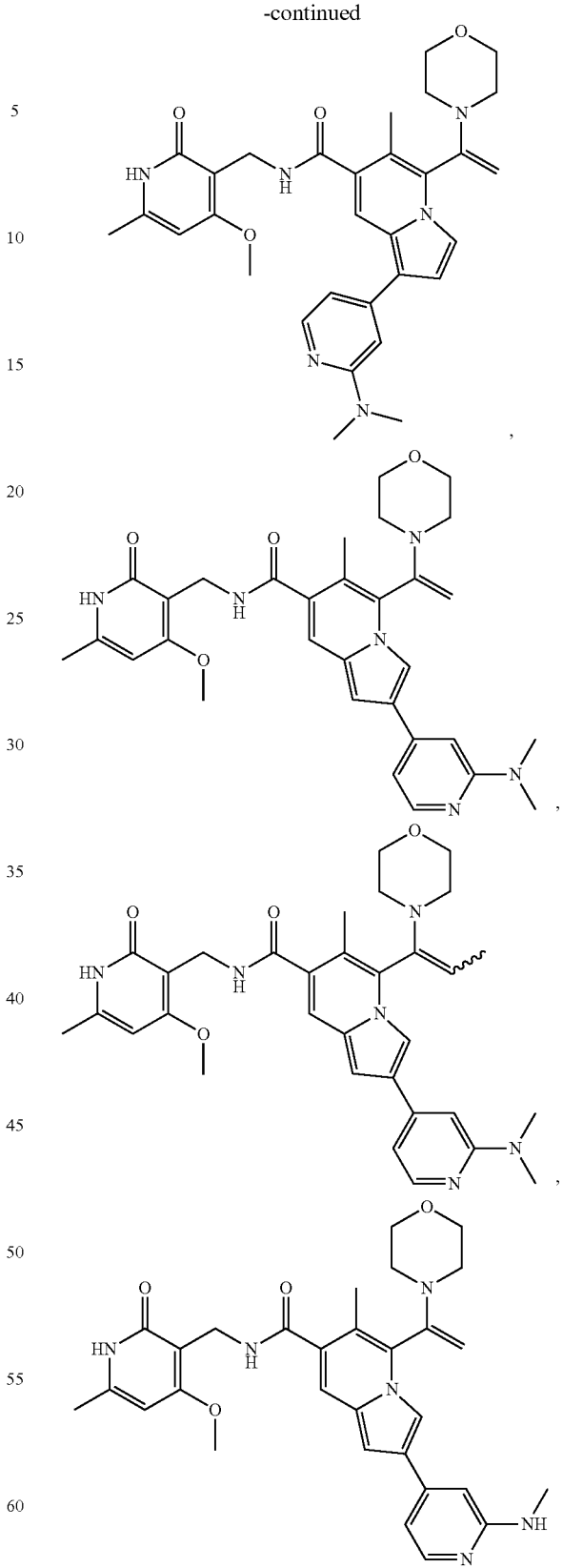
In another preferred embodiment, the indolizine compound represented by Formula I is selected from the following compounds:

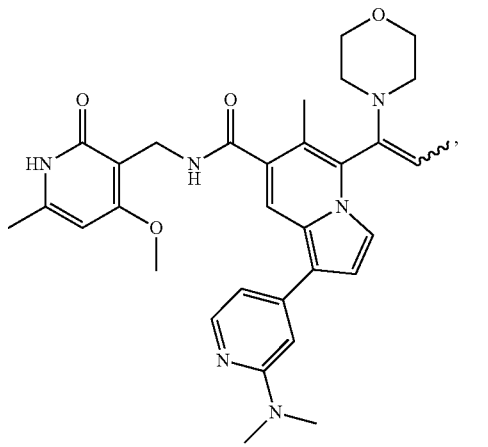
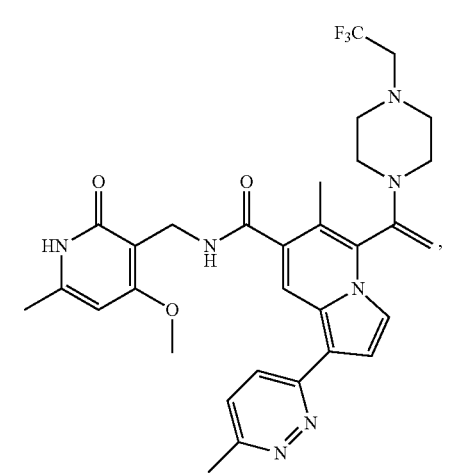
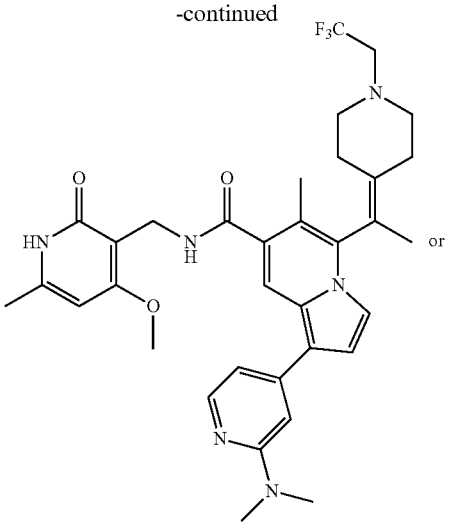
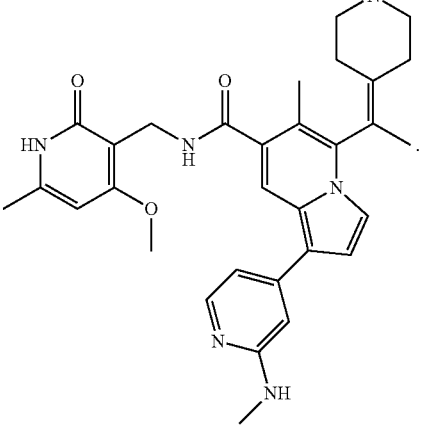
In the second aspect, the present invention provides a method for preparing the indolizine compound represented by Formula I or the pharmaceutically acceptable salt thereof, the method comprising one of the following methods:
Method I:
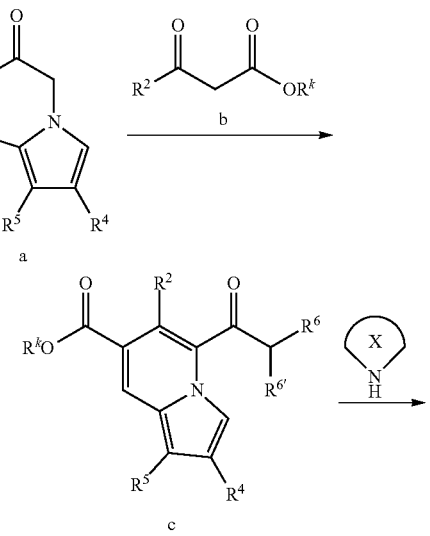

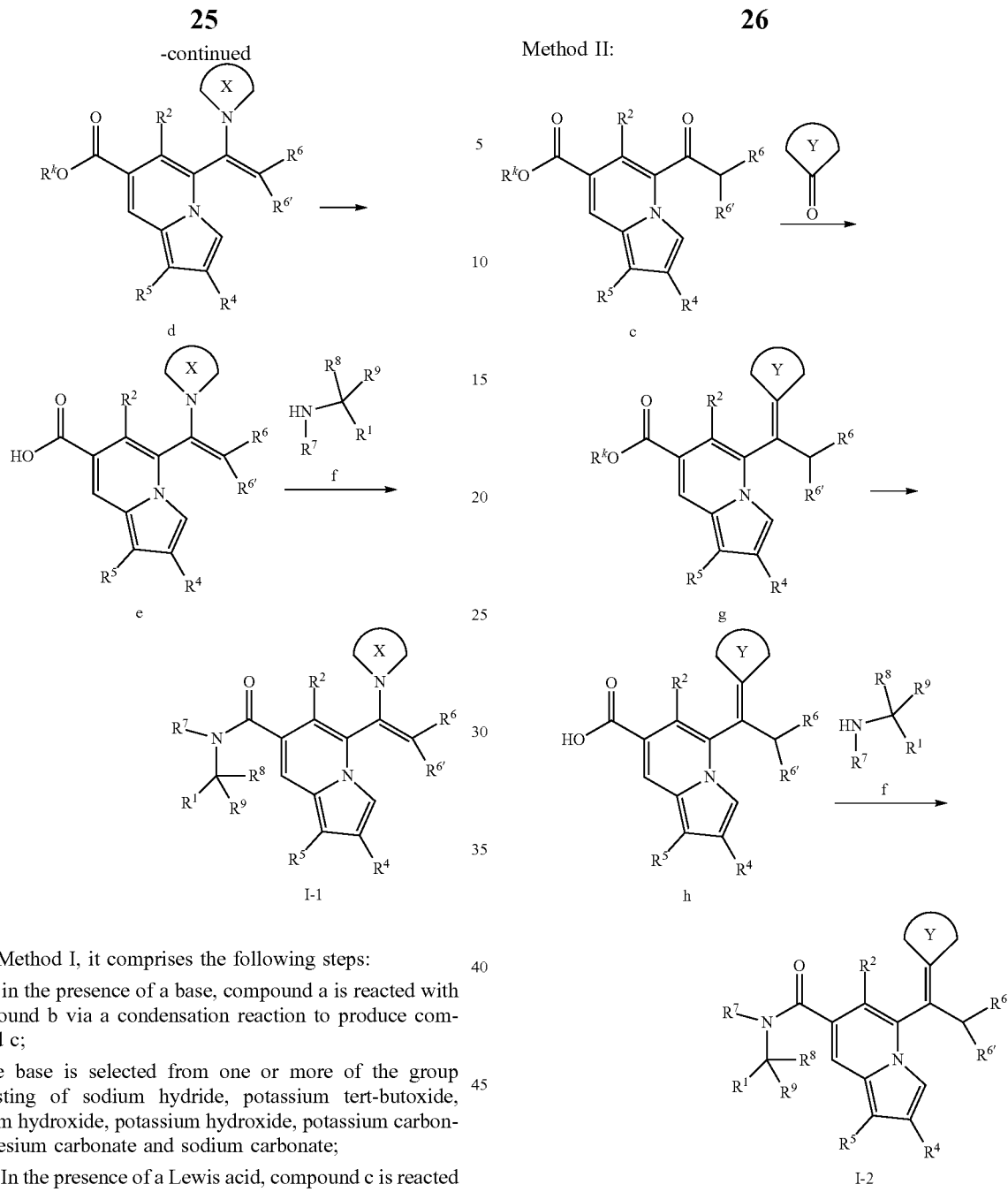

In Method I, it comprises the following steps:

(1) in the presence of a base, compound a is reacted with compound b via a condensation reaction to produce compound c;

The base is selected from one or more of the group consisting of sodium hydride, potassium tert-butoxide, sodium hydroxide, potassium hydroxide, potassium carbonate, cesium carbonate and sodium carbonate;

(2) In the presence of a Lewis acid, compound c is reacted with secondary amine via dehydration reaction to produce enamine compound d;

The Lewis acid is selected from one or more of the group consisting of titanium tetrachloride, tetraethyl titanate, tetraisopropyl titanate, boron trifluoride, copper chloride and aluminum trichloride;

(3) Compound d is hydrolyzed to produce compound e;

(4) Compound e is reacted with amine f via condensation reaction to produce compound I-1, Wherein, $R^1$, $R^2$, $R^4$, $R^5$, $R^6$, $R^{6'}$, $R^7$, $R^8$ and $R^9$ are defined as above, and $R^k$ is a C1-C4 linear or branched alkyl group; circle X is an optionally substituted 4-7 membered saturated or unsaturated heterocyclic group, and the heterocyclic group contains at least one N atom, and the optional substituent thereof is defined as the substituent in X as described above.

In Method II, it comprises the following steps:

(5) In the presence of titanium trichloride or titanium tetrachloride and a reducing agent, compound c is reacted with the corresponding ketone via McMurry reaction in an inert solvent to produce compound g;

The reducing agent is selected from one or more of the group consisting of lithium, sodium, magnesium, zinc, lithium aluminum hydride and zinc-copper couple; the inert solvent is selected from one or more the group consisting of tetrahydrofuran, 2-methyltetrahydrofuran, 1,4-dioxane, methylene chloride, chloroform, carbon tetrachloride and ethyl acetate;

(6) Compound g undergoes a hydrolysis reaction to produce compound h;

(7) compound g is reacted with amine f via condensation reaction to produce compound 1-2;

Wherein, $R^1$, $R^2$, $R^4$, $R^5$, $R^6$, $R^{6'}$, $R^7$, $R^8$ and $R^9$ are defined as above, and $R^k$ is a C1-C4 linear or branched alkyl group; circle Y is an optionally substituted saturated or unsaturated 4-7 membered cyclic hydrocarbyl group or optionally substituted 4-7 membered saturated or unsaturated heterocyclic group, and the heterocyclic group contains 1-2 heteroatoms selected from O, N, S and P, and the optional substituent thereof is defined as the substituent in X as described above.

In the third aspect, the present invention provides a pharmaceutical composition including:

(1) the indolizine compound represented by formula I, the pharmaceutically acceptable salt, enantiomer, diastereomer, tautomer, solvate, polymorph or prodrug thereof as described above; and (2) a pharmaceutically acceptable carrier.

Preferably, the pharmaceutical composition further includes other pharmaceutically acceptable therapeutic agents, especially other anti-tumor drugs. The therapeutic agents include but are not limited to: anti-tumor drugs that act on the chemical structure of DNA, such as cisplatin; anti-tumor drugs that affect nucleic acid synthesis, such as methotrexate (MTX), 5-fluorouracil (5FU), etc.; anti-tumor drugs that affect nucleic acid transcription, such as doxorubicin, epirubicin, aclacinomycin, mithramycin, etc.; anti-tumor drugs that affect tubulin synthesis, such as paclitaxel, vinorelbine, etc.; aromatase inhibitors, such as aminoglutethamide, Lentaron, Letrozole, Arimidex, etc.; cell signaling pathway inhibitors, such as epidermal growth factor receptor inhibitors including Imatinib, Gefitinib, Erlotinib, Lapatinib, etc.

In the fourth aspect, the present invention provides uses of the indolizine compound represented by formula I, the pharmaceutically acceptable salt, enantiomer, diastereomer, tautomer, solvate, polymorph or prodrug thereof as described above, the uses are selected from the group consisting of:

(a) Preparing drugs for preventing or treating diseases associated with mutation, activity or expression level of EZH1/2;

(b) Non-therapeutically inhibiting the activity of EZH1/2 and its mutants in vitro; and/or (c) Non-therapeutically inhibiting tumor cell proliferation in vitro.

In a preferred embodiment, the diseases associated with mutation, activity or expression level of EZH1/2 are selected from the group consisting of tumors and autoimmune diseases.

In another preferred embodiment, the diseases associated with mutation, activity or expression level of EZH1/2 are selected from the group consisting of B-cell lymphoma, malignant rhabdomyosarcoma, synovial sarcoma, breast cancer, colorectal cancer, endometrioma, stomach cancer, liver cancer, kidney cancer, lung cancer, melanoma, ovarian cancer, pancreatic cancer, prostate cancer, nasopharyngeal cancer and bladder cancer.

It should be understood that, within the scope of the present invention, the above technical features of the present invention and the technical features specifically described below (e.g., in the examples) can be combined with each other, thereby forming new or preferred technical solutions. For the sake of brevity, they are not described in details herein.

Explanations of Terms

All technical and scientific terms used herein have the same meaning as commonly understood by those skilled in the art to which this invention pertains, unless otherwise defined.

As used herein, when being used with specifically recited values, the term "about" means that the value can vary from the recited value by no more than 1%. For example, as used herein, the expression "about 100" includes all values between 99 and 101 (e.g., 99.1, 99.2, 99.3, 99.4, etc.).

As used herein, the terms "containing" or "including (comprising)" may represent an open, semi-closed, and closed expression. In other words, the terms also include "consisting essentially of" or "consisting of".

Definitions of Functional Groups

Definitions of standard chemical terms can be found in references (including Carey and Sundberg "ADVANCED ORGANIC CHEMISTRY 4TH ED." Vols. A (2000) and B (2001), Plenum Press, New York). Unless otherwise stated, within the technical scope of the art, conventional methods, such as mass spectrometry, NMR, IR, and UV/VIS spectroscopy, and pharmacological methods are applied in the present application. Unless specific definitions are given, the terms used in the description related to analytical chemistry, organic synthetic chemistry, and drugs and medicinal chemistry are known in the art. Standard techniques may be used in chemical synthesis, chemical analysis, pharmaceutical preparation, formulation and delivery, and treatment of patients. For example, reactions and purifications can be carried out according to manufacturer's instructions for a kit, or in a manner well known in the art or according to the description of the present invention. In general, the above-mentioned techniques and methods can be implemented according to conventional methods well known in the art with reference to the description in a number of summary and more specific documents cited or discussed in this specification. In this specification, groups and substituents thereof can be selected by those skilled in the art to provide stable structural moieties and compounds.

When a substituent is presented by a general chemical formula written from left to right, the substituent also includes the chemically equivalent substituent obtained when the structural formula is written from right to left. For example, —$CH_2O$— is equivalent to —$OCH_2$—.

The subtitles used herein are merely for the purpose of organizing sections and they should not be interpreted as for limiting the subject matter. All documents or parts cited in this application, including but not limited to patents, patent applications, articles, books, operating manuals and papers, are incorporated by reference in their entirety.

Some chemical groups defined herein are preceded by simplified symbols to indicate the total number of carbon atoms present in the group. For example, C1-C6 alkyl means an alkyl group as defined below having a total of 1 to 6 carbon atoms. The total number of carbon atoms in the simplified symbol does not include carbons that may be present in the substituent(s) of such group.

In addition to the foregoing, unless otherwise specified, the following terms, when used in the description and claims of this application, have the meanings as below.

In the present application, the term "halogen" means fluorine, chlorine, bromine or iodine.

"Hydroxy" means —OH group.

"Hydroxyalkyl" means an alkyl group as defined below substituted by a hydroxy group (—OH).

"Carbonyl" means —C(═O)— group.

"Nitro" means —$NO_2$.

"Cyano" means —CN.

"Amino" means —$NH_2$.

"Substituted amino" means an amino group substituted with one or two alkyl groups, alkylcarbonyl groups, aralkyl groups, heteroaralkyl groups as defined below, for example, monoalkylamino, dialkylamino, alkyl amido, aralkylamino, heteroaralkylamino.

"Carboxyl" means —COOH.

In the present application, as a group or a part of other groups (for example, used in halogen-substituted alkyl groups and the like), the term "alkyl" means a fully saturated linear or branched hydrocarbon chain group, which consists of only carbon atoms and hydrogen atoms, having, for example, 1 to 12 (preferably 1 to 8, more preferably 1 to 6) carbon atoms, and is connected to the other part of the molecule by a single bond. Its examples include, but are not limited to methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl and so on. In the present invention, the term "alkyl" means an alkyl group containing 1 to 6 carbon atoms.

In the present application, as a group or a part of other groups, the term "alkenyl" means a linear or branched hydrocarbon chain group containing at least one double bond, which consists of only carbon and hydrogen atoms, having, for example, 2 to 14 (preferably 2 to 10, more preferably 2 to 6) carbon atoms and is connected to the other part of the molecule by a single bond. Its examples include but are not limited to vinyl, propenyl, allyl, but-1-enyl, but-2-enyl, pent-1-enyl, pent-1,4-dienyl, etc.

In the present application, as a group or a part of other groups, the term "cyclic hydrocarbyl group" means a stable non-aromatic monocyclic or polycyclic hydrocarbyl group consisting only of carbon atoms and hydrogen atoms, which may include fused ring system, bridge ring system or spiro ring system, having 3 to 15 carbon atoms, preferably 3 to 10 carbon atoms, more preferably 3 to 8 carbon atoms, and it may be saturated or unsaturated and is connected to the other part of a molecule by a single bond via any suitable carbon atom. Unless otherwise specified in this specification, the carbon atoms in the cyclic hydrocarbyl group may be optionally oxidized. Examples of cycloalkyl include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-pentalenyl, etc.

In the present application, as a group or a part of other groups, the term "heterocyclic group" means a stable 3- to 20-membered non-aromatic cyclic group consisting of 2 to 14 carbon atoms and 1 to 6 heteroatoms selected from nitrogen, phosphorus, oxygen and sulfur. Unless otherwise specified in the specification, the heterocyclic group may be a monocyclic, bicyclic, tricyclic ring system or a ring system with even more rings, which may include a fused ring system, a bridge ring system or a spiro ring system; The nitrogen, carbon or sulfur atoms in the heterocyclic group can be optionally oxidized; the nitrogen atom therein can be optionally quaternized; and the heterocyclic group can be partially or fully saturated. The heterocyclic group may be connected to the other part of the molecule by a single bond via a carbon atom or a heteroatom. In a heterocyclic group containing a fused ring, one or more rings may be an aryl group or a heteroaryl group as defined below, provided that it is connected to the other part of the molecule via a non-aromatic ring atom. For the purposes of the present invention, the heterocyclic group is preferably a stable 4- to 11-membered non-aromatic monocyclic, bicyclic, bridged ring or spiro ring group containing 1 to 3 heteroatoms selected from nitrogen, oxygen and sulfur, more preferably, it is a stable 4- to 8-membered non-aromatic monocyclic, bicyclic, bridged ring or spiro ring group containing 1 to 3 heteroatoms selected from nitrogen, oxygen and sulfur. Examples of the heterocyclic group include, but are not limited to: pyrrolidinyl, morpholinyl, piperazinyl, homopiperazinyl, piperidinyl, thiomorpholinyl, 2,7-diaza-spiro[3.5]nonan-7-yl, 2-oxa-6-aza-spiro[3.3]heptane-6-yl, 2,5-diaza-bicyclo[2.2.1]heptan-2-yl, azetidyl, pyranyl, tetrahydropyranyl, thiopyranyl, tetrahydrofuranyl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isoxazolidinyl, dihydroindolyl, octahydroindolyl, octahydroisoindolyl, pyrrolidinyl, pyrazolidinyl, phthalimido group, etc.

In the present application, as a group or a part of other groups, the term "aryl" means a conjugated hydrocarbon ring system group having 6 to 18 carbon atoms (preferably having 6 to 10 carbon atoms). For the purposes of the present invention, an aryl group may be a monocyclic, bicyclic, tricyclic ring system or a ring system with even more rings, or it may be fused with a cycloalkyl or heterocyclic group as defined above, provided that the aryl group is connected to the other part of the molecule by a single bond via atoms on the aromatic ring. Examples of the aryl group include, but are not limited to, phenyl, naphthyl, anthracenyl, phenanthrenyl, fluorenyl, 2,3-dihydro-1H-isoindolyl, 2-benzoxazolinone, 2H-1,4-benzoxazine-3(4H)-one-7-yl and the like.

In the present application, the term "aralkyl" means an alkyl group as defined above substituted with an aryl group as defined above.

In the present application, as a group or a part of other groups, the term "heteroaryl" means a 5- to 16-membered conjugated ring system group having 1 to 15 carbon atoms (preferably having 1 to 10 carbon atoms) and 1 to 6 heteroatoms selected from nitrogen, oxygen and sulfur within the ring. Unless otherwise specified in the specification, the heteroaryl group may be a monocyclic, bicyclic, tricyclic ring system or a ring system with even more rings, and may also be fused with a cycloalkyl or heterocyclic group as defined above, provided that the heteroaryl group is connected to the other part of the molecule by a single bond via atoms on the aromatic ring. The nitrogen, carbon or sulfur atoms in the heteroaryl group may be optionally oxidized; the nitrogen atom may be optionally quaternized. For the purposes of the present invention, the heteroaryl group is preferably a stable 5- to 12-membered aromatic group containing 1 to 5 heteroatoms selected from nitrogen, oxygen and sulfur, and more preferably, a stable 5- to 10-membered aromatic group containing 1 to 4 heteroatoms selected from nitrogen, oxygen and sulfur, or, a 5- to 6-membered aromatic group containing 1 to 3 heteroatoms selected from nitrogen, oxygen and sulfur. Examples of the heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furanyl, pyrrolyl, triazolyl, tetrazolyl, triazinyl, indolizinyl, isoindolyl, indazolyl, isoindazolyl, purinyl, quinolinyl, isoquinolinyl, diazonaphthyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxtriazolyl, cinnolinyl, quinazolinyl, phenylthio group, indolizinyl, o-phenanthrolinyl, isoxazolyl, phenoxazinyl, phenothiazinyl, 4,5,6,7-tetrahydrobenzo[b]thienyl, naphthopyridyl, [1,2,4]triazolo[4,3-b]pyridazinyl, [1,2,4]triazolo[4,3-a]pyrazinyl, [1,2,4]triazolo[4,3-c]pyrimidinyl, [1,2,4]triazolo[4,3-a]pyridinyl, imidazo[1,2-a]pyridinyl, imidazo[1,2-b]pyridazinyl, imidazo[1,2-a]pyrazinyl and the like.

In the present application, the term "heteroaralkyl" means an alkyl group as defined above substituted with a heteroaryl as defined above.

In the present application, "optionally" means that the event or condition described thereafter may or may not occur, and the expression includes both cases where the event or condition occurs or not. For example, "optionally substituted aryl" means that the aryl is substituted or unsubstituted, and the expression includes both substituted aryl and unsubstituted aryl. For example, where no substituent is explicitly listed, the term "substituted" or "substituted by or with . . . " as used herein means that one or more hydrogen atoms on a given atom or group are independently replaced by one or more, for example 1, 2, 3 or 4 substituents, the substituents are independently selected from the group consisting of deuterium (D), halogen, —OH, mercapto, cyano, —$CD_3$, —$C_1$-$C_6$ alkyl (preferably $C_{1-3}$ alkyl), $C_2$-$C_6$ alkenyl, $C_2$-$C_6$ alkynyl, cycloalkyl (preferably 3-8 membered cycloalkyl), aryl, heterocyclic group (preferably 3-8 membered heterocyclic group), heteroaryl, aryl $C_1$-$C_6$ alkyl-, heteroaryl $C_1$-$C_6$ alkyl-, $C_1$-$C_6$ haloalkyl-, —$OC_1$-$C_6$ alkyl (preferably —$OC_1$-$C_3$ alkyl), —$OC_2$-$C_6$ alkenyl, —$OC_1$-$C_6$ alkyl phenyl, —$C_1$-$C_6$ alkyl-OH (preferably —$C_1$-$C_4$ alkyl-OH), —$C_1$-$C_6$ alkyl-SH, —$C_1$-$C_6$ alkyl-O—$C_1$-$C_6$ alkyl, —$OC_1$-$C_6$ haloalkyl, —$NH_2$, —$C_1$-$C_6$ alkyl-$NH_2$ (preferably —$C_1$-$C_3$ alkyl-$NH_2$), —N($C_1$-$C_6$ alkyl)$_2$ (preferably —N($C_1$-$C_3$ alkyl)$_2$), —NH($C_1$-$C_6$ alkyl) (preferably —NH($C_1$-$C_3$ alkyl)), —N($C_1$-$C_6$ alkyl) ($C_1$-$C_6$ alkylphenyl), —NH($C_1$-$C_6$ alkylphenyl), nitro, —C(O)—OH, —C(O)$OC_1$-$C_6$ alkyl (preferably —C(O)$OC_1$-$C_3$ alkyl), —CONRiRii (where Ri and Rii are H, D and $C_{1-6}$ alkyl, preferably $C_{1-3}$ alkyl), —NHC(O)($C_1$-$C_6$ alkyl), —NHC(O)(phenyl), —N($C_1$-$C_6$ alkyl)C(O)($C_1$-$C_6$ alkyl), —N($C_1$-$C_6$ alkyl)C(O)(phenyl), —C(O)$C_1$-$C_6$ alkyl, —C(O)heteroaryl (preferably —C(O)-5-7-membered heteroaryl), —C(O)$C_1$-$C_6$ alkylphenyl, —C(O)$C_1$-$C_6$ haloalkyl, —OC(O)$C_1$-$C_6$ alkyl (preferably —OC(O)$C_1$-$C_3$ alkyl), —S(O)$_2$—$C_1$-$C_6$ alkyl, —S(O)—$C_1$-$C_6$ alkyl, —S(O)$_2$-phenyl, —S(O)$_2$—$C_1$-$C_6$ haloalkyl, —S(O)$_2NH_2$, S(O)$_2$NH($C_1$-$C_6$ alkyl), —S(O)$_2$NH(phenyl), —NHS(O)$_2$($C_1$-$C_6$ alkyl), —NHS(O)$_2$(phenyl) and —NHS(O)$_2$($C_1$-$C_6$ haloalkyl), wherein each of the alkyl, cycloalkyl, phenyl, aryl, heterocyclic group and heteroaryl is optionally further substituted with one or more substituents selected from the group consisting of halogen, —OH, —$NH_2$, cycloalkyl, 3-8 membered heterocyclic group, $C_1$-$C_4$ alkyl, $C_1$-$C_4$ haloalkyl-, —$OC_1$-$C_4$ alkyl, —$C_1$-$C_4$ alkyl-OH, —$C_1$-$C_4$ alkyl-O—$C_1$-$C_4$ alkyl, —$OC_1$-$C_4$ haloalkyl, cyano, nitro, —C(O)—OH, —C(O)$OC_1$-$C_6$ alkyl, —CON($C_1$-$C_6$ alkyl)$_2$, —CONH($C_1$-$C_6$ alkyl), —$CONH_2$, —NHC(O)($C_1$-$C_6$ alkyl), NH($C_1$-$C_6$ alkyl)C(O)($C_1$-$C_6$ alkyl), —$SO_2$($C_1$-$C_6$ alkyl), —$SO_2$(phenyl), —$SO_2$($C_1$-$C_6$ haloalkyl), —$SO_2NH_2$, —$SO_2$NH($C_1$-$C_6$ alkyl), —$SO_2$NH(phenyl), —$NHSO_2$($C_1$-$C_6$ alkyl), —$NHSO_2$(phenyl) and —$NHSO_2$ ($C_1$-$C_6$ haloalkyl). When one atom or group is substituted with multiple substituents, the substituents may be the same or different from each other. As used herein, the terms "moiety", "structural moiety", "chemical moiety", "group", "chemical group" mean a specific segment or functional group in a molecule. Chemical moieties are generally considered to be chemical entities embedded or attached to molecules.

"Stereoisomer" refers to those compounds which are composed of the same atoms, bonded by the same bond, but have different three-dimensional structures. The present invention will cover various stereoisomers and mixtures thereof.

When the compound of the present invention contains an olefinic double bond, unless otherwise specified, the compounds of the present invention are intended to include E- and Z-geometric isomers.

"Tautomer" means an isomer formed by the transfer of protons from one atom in a molecule to another atom of the same molecule. All tautomeric forms of the compounds of the invention are also to be included within the scope of the invention.

The compounds or pharmaceutically acceptable salts thereof in the present invention may contain one or more chiral carbon atoms, and thus they may have enantiomers, diastereomers, and other stereoisomeric forms. Each chiral carbon atom can be defined as (R)— or (S)— according to stereochemistry. The present invention is intended to include all possible isomers, as well as their racemates and optically pure forms. For the preparation of the compounds of the present invention, racemates, diastereomers or enantiomers can be selected as starting materials or intermediates. Optically active isomers can be prepared using chiral synthons or chiral reagents, or resolved using conventional techniques, for example, using methods such as crystallization and chiral chromatography.

Conventional techniques for preparing/isolating individual isomers include chiral synthesis from suitable optically pure precursors, or resolution of racemates (or racemates of salts or derivative) using, for example, chiral high performance liquid chromatography, for example, see Gerald Gübitz and Martin G. Schmid (Eds.), Chiral Separations, Methods and Protocols, Methods in Molecular Biology, Vol. 243, 2004; A M Stalcup, Chiral Separations, *Annu. Rev. Anal. Chem.* 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, *Acc. Chem. Res.* 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" means a salt formed with an inorganic acid or an organic acid that can retain the biological activity of the free base without other side effects. Inorganic acid salts include but are not limited to hydrochloride, hydrobromide, sulfate, nitrate, phosphate, etc.; organic acid salts include but are not limited to formate, acetate, 2,2-dichloroacetate, trifluoroacetate, propionate, hexanoate, caprylate, caprate, undecylenate, glycolate, gluconate, lactate, sebacate, adipicate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzenesulfonate, p-toluenesulfonate, alginate, ascorbate, salicylate, 4-aminosalicylate, naphthalenedisulfonate, etc. These salts can be prepared by methods known in the art.

"Pharmaceutically acceptable base addition salt" means a salt formed with an inorganic base or an organic base that can retain the biological activity of the free acid without other side effects. Salts derived from inorganic bases include, but are not limited to, sodium salt, potassium salt, lithium salt, ammonium salt, calcium salt, magnesium salt, iron salt, zinc salt, copper salt, manganese salt, aluminum salt, and the like. Preferred inorganic salts are ammonium salt, sodium salt, potassium salt, calcium salt and magnesium salt. Salts derived from organic bases include, but are not limited to, the following salts: primary amines, secondary amines, and tertiary amines, substituted amines, including natural substituted amines, cyclic amines, and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline, and caffeine. These salts can be prepared by methods known in the art.

In the present application, "pharmaceutical composition" means a formulation of a compound of the present invention and a medium generally accepted in the art for delivering a biologically active compound to a mammal (e.g., a human). The medium includes a pharmaceutically acceptable carrier. The pharmaceutical composition is used for the purpose of promoting the administration to living organisms, facilitating the absorption of active ingredients and thus promoting the exertion of the biological activity thereof.

The term "pharmaceutically acceptable" used herein means a substance (such as a carrier or diluent) that does not affect the biological activity or properties of the compound of the present invention, and it is relatively non-toxic, that is, the substance can be administered to an individual without causing harmful effect on the organism or without interacting with any components contained in the composition in an undesirable manner.

In the present application, "pharmaceutically acceptable excipients" include, but are not limited to, any adjuvants, carriers, excipients, glidants, sweeteners, diluents, preservatives, dyes/colorants, flavoring agents, surfactants, wetting agents, dispersants, suspending agents, stabilizers, isotonic agents, solvents or emulsifiers that are approved by the relevant government administration departments to be acceptable for human or domestic animal use.

The "tumors" in the present invention include, but are not limited to diseases such as glioma, sarcoma, melanoma, articular chondroma, cholangiocarcinoma, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanoma, kidney cancer, oral cancer.

The terms "preventive", "prevention" and "preventing" used herein means reducing the likelihood of the occurrence or worsening of a disease or disorder in a patient.

The term "treatment" and other similar synonyms used herein include the following meanings:

(i) preventing the occurrence of a disease or disorder in mammals, especially when such mammals are susceptible to the disease or disorder but have not been diagnosed with the disease or disorder;

(ii) Inhibiting a disease or disorder, that is, repressing its development;

(iii) Alleviating a disease or disorder, that is, resolving the condition of the disease or disorder; or (iv) Relieving the symptoms caused by the disease or disorder.

The terms "effective amount", "therapeutically effective amount" or "pharmaceutically effective amount" used herein means the amount of at least one agent or compound that is sufficient to alleviate one or more symptoms of the disease or disorder being treated to some extent after its administration. The results may be the reduction and/or remission of signs, symptoms or causes, or any other desired changes in the biological system. For example, an "effective amount" for treatment is the amount of a composition comprising a compound disclosed herein required to provide a clinically significant disease relief effect. Techniques such as dose escalation tests can be used to determine the effective amount suitable for any individual case.

The term "administering", "administration", and "application" and the like used herein means a method capable of delivering a compound or composition to a desired site for biological action. These methods include, but are not limited to, oral route, transduodenal route, parenteral injection (including intravenous, subcutaneous, intraperitoneal, intramuscular, intraarterial injection or infusion), local administration, and transrectal administration. Techniques that can be used for administering the compounds and methods described herein are well known to those skilled in the art, such as those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

The terms "pharmaceutical combination", "combination of drugs", "combined administration", "administration of other treatments", "administration of other therapeutic agents", etc. used herein mean pharmaceutical treatments obtained by mixing or combining more than one active ingredient, they include fixed and unfixed combinations of active ingredients. The term "fixed combination" means simultaneous administration of at least one compound described herein and at least one synergistic agent to a patient in the form of a single entity or a single dosage form. The term "unfixed combination" means simultaneous administration, co-administration, or sequential administration at variable intervals of at least one compound described herein and at least one synergistic agent to a patient in the form of separate entities. These are also applied to cocktail therapy, such as the administration of three or more active ingredients.

Those skilled in the art should also understand that in the method described below, a functional group in an intermediate compound may need to be protected by an appropriate protecting group. Such functional groups include hydroxyl, amino, mercapto and carboxyl group. Suitable protecting groups for hydroxyl group include trialkylsilyl or diarylalkylsilyl (e.g., tert-butyldimethylsilyl, tert-butyldiphenylsilyl or trimethylsilyl), tetrahydropyranyl, benzyl and the like. Suitable protecting groups for amino, amidino and guanidino group include t-butoxycarbonyl, benzyloxycarbonyl and the like. Suitable protecting groups for mercapto group include —C(O)—R" (where R" is alkyl, aryl or aralkyl), p-methoxybenzyl, trityl and the like. Suitable protecting groups for carboxyl group include alkyl, aryl or aralkyl esters.

Protecting groups can be introduced and removed according to standard techniques known to those skilled in the art and those as described herein. The use of protecting groups is detailed in Greene, T. W. and P. G. M. Wuts, Protective Groups in Organi Synthesis, (1999), 4th Ed., Wiley. The protective group may also be a polymer resin.

Advantageous Effects

1. An indolizine compound represented by formula I or a pharmaceutically acceptable salt thereof is provided.
2. A pharmaceutical composition with a novel structure for preventing and treating diseases associated with EZH1/2 mutation is provided.

DETAILED EMBODIMENTS

The present invention will be further described below with reference to the specific examples. It should be understood that these examples are only used to explain the present invention and not intended to limit the scope of the present invention. In the following examples, the experimental methods without specific conditions were implemented generally under the conventional conditions or the conditions recommended by the manufacturer. Unless stated otherwise, percentages and parts represent percentages by weight and parts by weight.

Unless otherwise specified, all of the experimental materials and reagents used in the following examples are commercially available.

In each example, $^1$H NMR was recorded on a Varian Mercury-400 nuclear magnetic resonance instrument, and the chemical shift was expressed in δ (ppm); the mass spectrum was recorded on Finnigan/MAT-95 (EI) and Finnigan LCQ/DECA and Micromass Ultra Q-TOF (ESI) mass spectrometer; 200-300 mesh silica gel was used for reversed-phase preparative HPLC separation.

In the following examples, the agents used are abbreviated as below or are represented by chemical formulas as below:

iPrOH: isopropanol; EtOH: ethanol; DCM: dichloromethane; TFA: trifluoroacetic acid; MeOH: methanol; NaOH: sodium hydroxide; HCl: hydrogen chloride; TEA: triethylamine; 1,4-dioxane; NaH: sodium hydride; H$_2$O: water; HATU: 2-(7-oxybenzotriazole)-N,N,N',N'-tetramethylurea hexafluorophosphate; DMF: N,N-dimethylformamide; THF: tetrahydrofuran; NBS: N-bromosuccinimide; MeCN: acetonitrile; DIPEA: N,N-diisopropylethylamine; DMSO: dimethyl sulfoxide; pyridine; ethyl acetate; K$_2$CO$_3$: potassium carbonate; Cs$_2$CO$_3$: cesium carbonate; Pd(dppf)Cl$_2$: [1,1'-bis(diphenylphosphino)ferrocene]dichloro palladium; KOAc: potassium acetate; LiOH: lithium hydroxide.

Example 1: Preparation of 1-(2-(dimethylamino) pyridin-4-yl)-N-((4-methoxy-6-methyl-2-oxo-1,2-dihydropyridin-3-yl)methyl)-6-methyl-5-(1-morpholinylpropyl-1-en-1-yl)indolizine-7-formamide

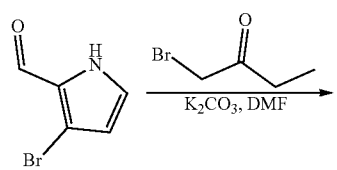

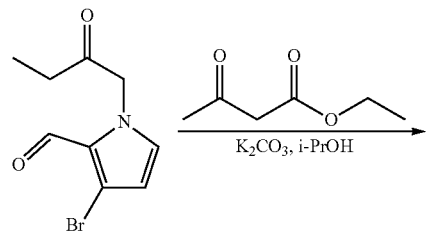

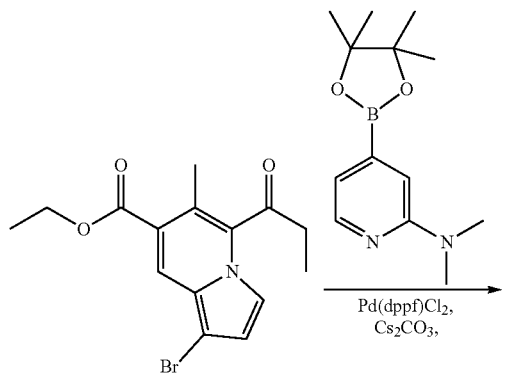

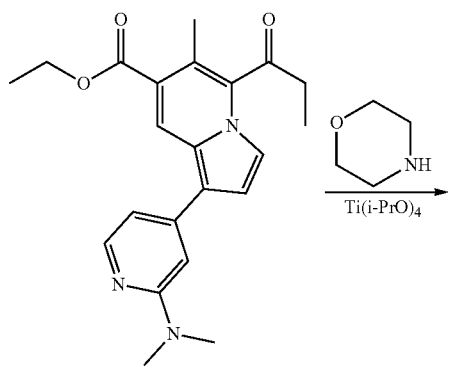

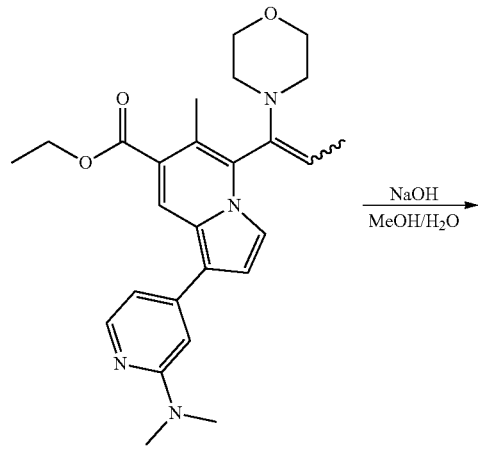

-continued

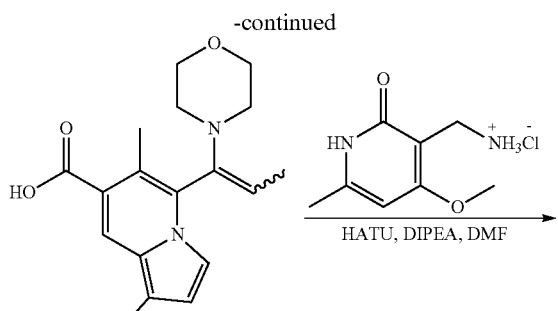

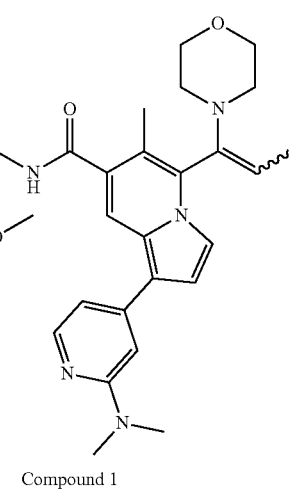

Compound 1

Step 1: Preparation of 3-bromo-1-(2-oxobutyl)-1H-pyrrole-2-carbaldehyde: 1-bromobutan-2-one (192 mg) and potassium carbonate (222 mg) were added successively to a solution of 3-bromo-1H-pyrrole-2-carbaldehyde (200 mg) (Please see WO2012029942 for its preparation) in DMF (5 ml), and the mixture was stirred overnight at room temperature. The reaction solution was extracted three times with ethyl acetate, washed successively with water and saturated brine. The organic phases were combined, and distilled under reduced pressure, and the crude product thus obtained was separated by a fast separation column (petroleum ether: ethyl acetate=10:1, v/v) to give a yellow solid (215 mg, yield: 76%). MS (ESI) m/z 216 [M+H–CHO]$^+$.

Step 2: Preparation of ethyl 1-bromo-6-methyl-5-propionylindolizine-7-carboxylate: ethyl acetate (345 mg) and potassium carbonate (182 mg) were added to a solution of 3-bromo-1-(2-oxopropyl)-1H-pyrrole-2-carbaldehyde (215 mg) in isopropanol (5 ml), respectively, and the resultant was reacted at 100° C. for 5 hours. The reaction solution was cooled and then filtered, washed with ethyl acetate, and the filtrate was concentrated under reduced pressure. The crude product thus obtained was separated by a fast separation column (petroleum ether: ethyl acetate=10:1, v/v) to give a yellow solid (83 mg, yield: 28%). MS (ESI) m/z 338 [M+H]$^+$.

Step 3: Preparation of ethyl 1-(2-(dimethylamino)pyridin-4-yl)-6-methyl-5-propionylindolizine-7-carboxylate: in a 100 mL single-necked flask under the protection of dried nitrogen, compounds ethyl 1-bromo-6-methyl-5-propionylindolizine-7-carboxylate (159 mg), N,N-dimethyl-5-(4,4,5,5-tetramethyl-1,3,2-dioxaborolan-2-yl)pyridin-2-amine (352 mg), Pd(dppf)Cl$_2$ (18 mg), cesium carbonate (308 mg) were added to a mixed solution of 1,4-dioxane and water (5:1, v/v). The system, being connected to a balloon filled with nitrogen and replaced with nitrogen for several times, was stirred overnight in an oil bath at 110° C. The reaction solution was extracted with dichloromethane (100 ml), washed with water (50 ml×2), and saturated brine (50 ml). The organic phase was dried over anhydrous sodium sulfate, filtered and concentrated to obtain a crude product. The crude product was purified by column chromatography (petroleum ether: ethyl acetate=3:1) to give a yellow-green solid (97 mg, yield: 54%). MS (ESI) m/z 380 [M+H]$^+$.

Step 4: Preparation of isopropyl 1-(2-(dimethylamino)pyridin-4-yl)-6-methyl-5-(1-morpholinylpropyl-1-en-1-yl)indoizine-7-carboxylate: In a reaction flask, 2 ml of morpholine and 1 ml of titanium tetraisopropoxide were added to ethyl 1-(2-(dimethylamino)pyridin-4-yl)-6-methyl-5-propionylindolizine-7-carboxylate (97 mg), the mixture was raised to 100° C. and stirred overnight. The reaction solution was cooled and then diluted with dichloromethane (15 ml), and 0.5 ml of water was added thereto. The resultant was concentrated under reduced pressure, and the residue was further added with 30 ml of dichloromethane and filtered. The filtrate was dried over anhydrous sodium sulfate, filtered and concentrated to give a yellow solid (110 mg, yield: 93%). MS (ESI) m/z 463 [M+H]$^+$.

Step 5: Preparation of 1-(2-(dimethylamino)pyridin-4-yl)-6-methyl-5-(1-morpholinylpropyl-1-en-1-yl)indoizine-7-carboxylic acid: a 2M of aqueous solution of sodium hydroxide (2.5 mL) was slowly added to a solution of isopropyl 1-(2-(dimethylamino)pyridin-4-yl)-6-methyl-5-(1-morpholinylpropyl-1-en-1-yl)indolizine-7-carboxylate (110 mg) in methanol (2.5 mL), the solution was raised to 60° C. and stirred overnight, and the reaction solution was neutralized with dilute hydrochloric acid (1M) to pH 5. The resultant was separated by a reversed-phase fast separation column (acetonitrile: water=1:4, v/v) to give a pale yellow-green solid (70 mg, yield: 70%). MS (ESI) m/z 421 [M+H]$^+$.

Step 6: Preparation of 1-(2-(dimethylamino)pyridin-4-yl)-N-((4-methoxy-6-methyl-2-oxo-1,2-dihydropyridine-3-yl)methyl)-6-methyl-5-(1-morpholinylpropyl-1-en-1-yl)indolizine-7-carboxamide: 3-(aminomethyl)-4-methoxy-6-picoline-2(1H)-one hydrochloride (41 mg) (see WO2015023915 for its synthesis), HATU (95 mg), diisopropylethylamine (51 mg) were successively added to a solution of 1-(2-(dimethylamino)pyridine-4-yl)-6-methyl-5-(1-morpholinylpropyl-1-en-1-yl)indolizine-7-carboxylic acid (70 mg) in N,N-dimethylformamide (2 ml), the solution was stirred overnight at room temperature. After preparation, separation and purification, a yellow solid was obtained (5 mg, yield: 9%). $^1$H NMR (400 MHz, CDCl$_3$) δ 8.06 (d, J=5.3 Hz, 1H), 7.89 (s, 1H), 7.86 (d, J=5.0 Hz, 1H), 7.38 (d, J=2.8 Hz, 1H), 6.97 (d, J=2.9 Hz, 1H), 6.74 (d, J=5.3 Hz, 1H), 6.63 (s, 1H), 5.86 (s, 1H), 5.01 (q, J=6.8 Hz, 1H), 4.66-4.51 (m, 2H), 3.89 (s, 3H), 3.71-3.58 (m, 4H), 3.05 (s, 6H), 2.84 (dd, J=14.6, 10.1 Hz, 4H), 2.35 (s, 3H), 2.15 (s, 3H), 1.40 (d, J=6.8 Hz, 3H); MS (ESI) m/z 571 [M+H]$^+$.

39

Example 2: Preparation of 1-(2-(dimethylamino)pyridin-4-yl)-N-((4-methoxy-6-methyl-2-oxo-1,2-dihydropyridin-3-yl)methyl)-6-methyl-5-(1-morpholinylvinyl)indolizine-7-formamide

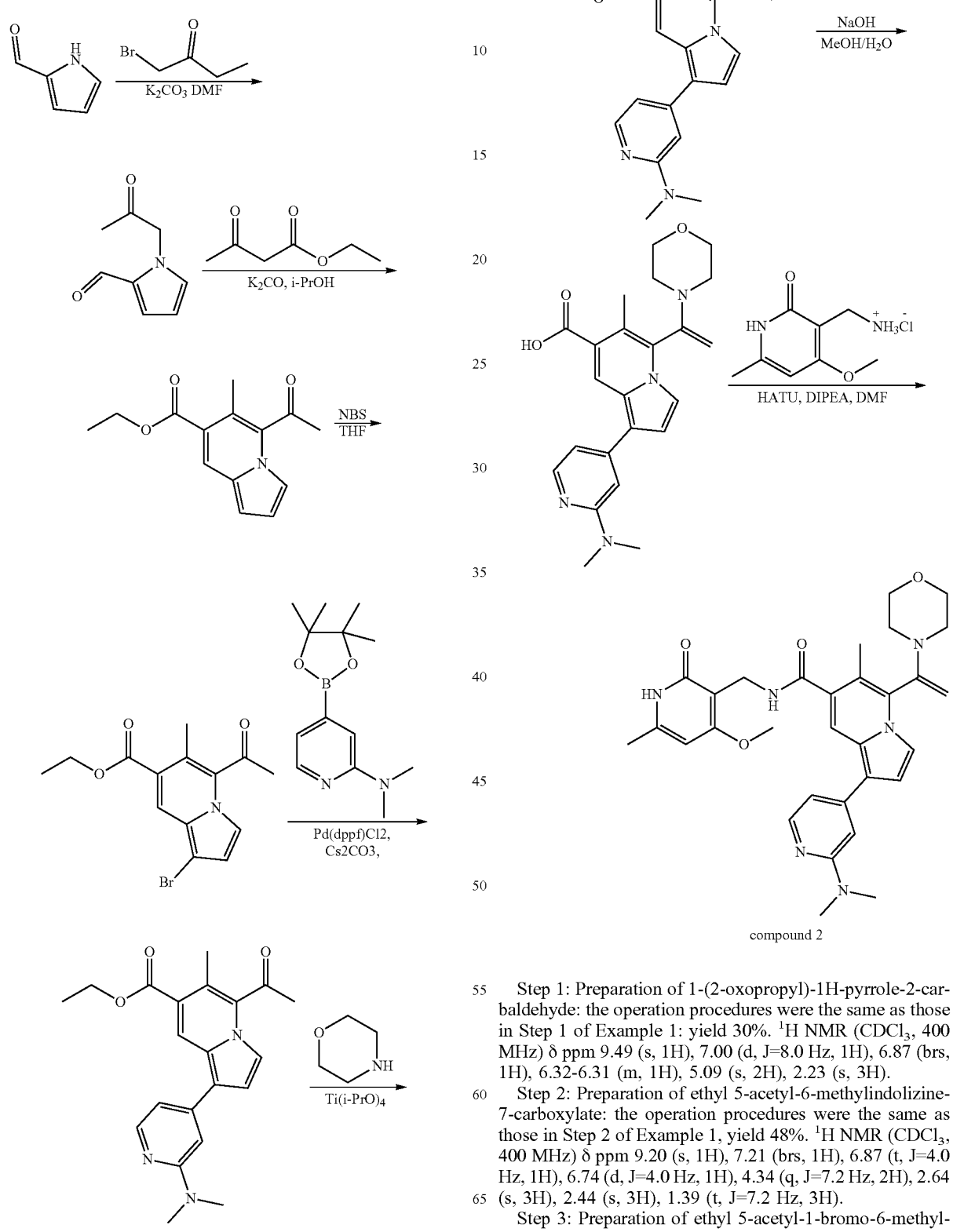

compound 2

Step 1: Preparation of 1-(2-oxopropyl)-1H-pyrrole-2-carbaldehyde: the operation procedures were the same as those in Step 1 of Example 1: yield 30%. $^1$H NMR (CDCl$_3$, 400 MHz) δ ppm 9.49 (s, 1H), 7.00 (d, J=8.0 Hz, 1H), 6.87 (brs, 1H), 6.32-6.31 (m, 1H), 5.09 (s, 2H), 2.23 (s, 3H).

Step 2: Preparation of ethyl 5-acetyl-6-methylindolizine-7-carboxylate: the operation procedures were the same as those in Step 2 of Example 1, yield 48%. $^1$H NMR (CDCl$_3$, 400 MHz) δ ppm 9.20 (s, 1H), 7.21 (brs, 1H), 6.87 (t, J=4.0 Hz, 1H), 6.74 (d, J=4.0 Hz, 1H), 4.34 (q, J=7.2 Hz, 2H), 2.64 (s, 3H), 2.44 (s, 3H), 1.39 (t, J=7.2 Hz, 3H).

Step 3: Preparation of ethyl 5-acetyl-1-bromo-6-methylindolizine-7-carboxylate: In a 100 ml dry single-necked flask, ethyl 5-acetyl-6-methylindolizine-7-carboxylate (500 mg, 2 mmol) was dissolved in 20 mL of tetrahydrofuran, and bromosuccinimide (320 mg, 1.8 mmol) was added in portions at 0° C., and the mixture was stirred at 0° C. for 20 min. The solvent was distilled off under reduced pressure to obtain a crude product. The crude product was separated by column chromatography (petroleum ether: ethyl acetate=20: 1, v/v) to give a yellow oily substance 141 mg, yield 26%. $^1$H NMR (CDCl$_3$, 400 MHz) δ ppm 8.15 (s, 1H), 7.17 (d, J=2.8 Hz, 1H), 6.89 (d, J=2.8 Hz, 1H), 4.37 (q, J=14 Hz, 2H), 2.63 (s, 3H), 2.44 (s, 3H), 1.42 (t, J=14 Hz, 3H).

Step 4: Preparation of ethyl 5-acetyl-1-(2-(dimethylamino)pyridin-4-yl)-6-methylindolizine-7-carboxylate: the operation procedures were the same as those in Step 3 of Example 1.

Step 5: Preparation of isopropyl 1-(2-(dimethylamino)pyridin-4-yl)-6-methyl-5-(1-morpholinylvinyl)indolizine-7-carboxylate: the operation procedures were the same as those in Step 4 of Example 1.

Step 6: Preparation of 1-(2-(dimethylamino)pyridin-4-yl)-6-methyl-5-(1-morpholinylvinyl)indolizine-7-carboxylic acid: the operation procedures were the same as those in Step 5 of Example 1.

Step 7: Preparation of 1-(2-(dimethylamino)pyridin-4-yl)-N-((4-methoxy-6-methyl-2-oxo-1,2-dihydropyridin-3-yl)methyl)-6-methyl-5-(1-morpholinylvinyl)indolizine-7-carboxamide: the operation procedures were the same as those in Step 6 of Example 1.

Example 3: Preparation of N-((4-methoxy-6-methyl-2-oxo-1,2-dihydropyridin-3-yl)methyl)-6-methyl-1-(6-methylpyridazin-3-yl)-5-(1-(4-(2,2,2-trifluoroethyl)piperazin-1-yl)vinyl)indolizine-7-carboxamide

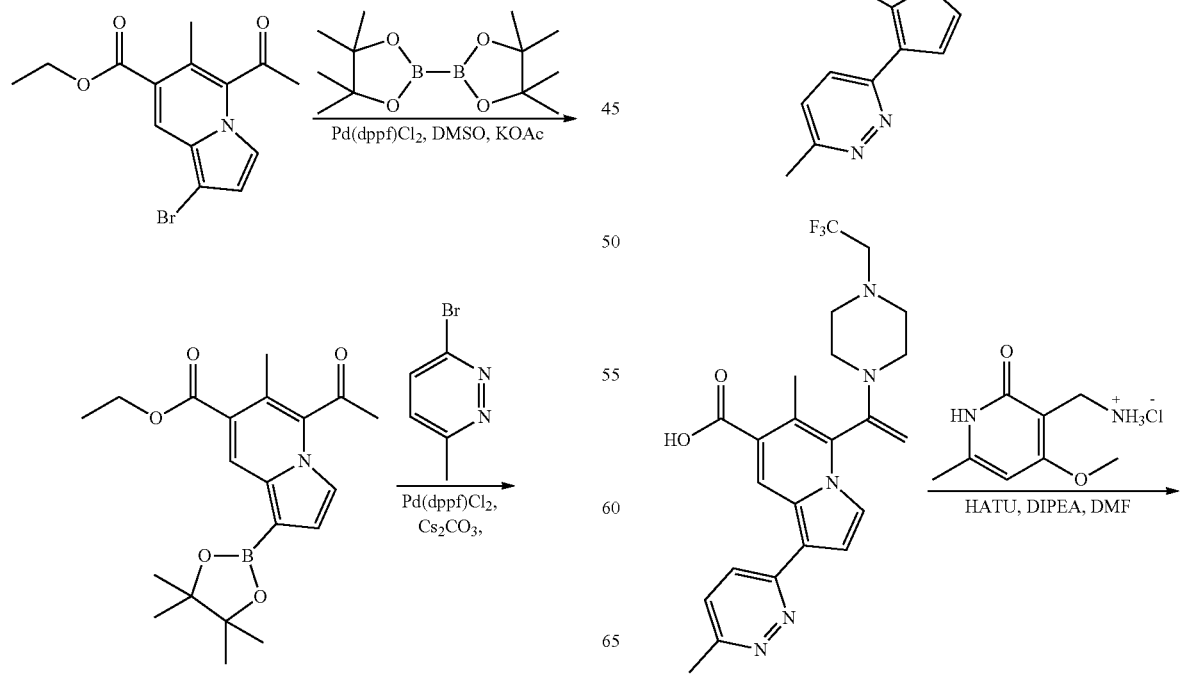

7.49 (d, J=5.7 Hz, 1H), 7.48 (s, 1H), 7.39 (d, J=3.0 Hz, 1H), 6.11 (s, 1H), 4.54 (s, 1H), 4.26 (d, J=4.6 Hz, 2H), 4.15 (s, 1H), 3.85 (s, 3H), 3.18 (q, J=10.0 Hz, 2H), 2.98-2.78 (m, 4H), 2.67-2.60 (m, 4H), 2.59 (s, 3H), 2.22 (s, 3H), 2.18 (s, 3H); MS (ESI) m/z 610 [M+H]$^+$.

Example 4: Preparation of 1-(2-(dimethylamino)pyridin-4-yl)-N-((4-methoxy-6-methyl-2-oxo-1,2-dihydropyridine-3-yl)methyl)-6-methyl-5-(1-(1-(2,2,2-trifluoroethyl)piperidin-4-alkenylene)ethyl)indolizine-7-formamide

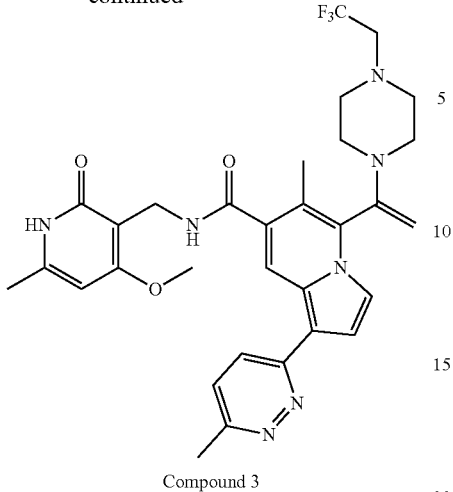

Compound 3

Step 1: Preparation of ethyl 5-acetyl-6-methyl-1-(4,4,5,5-tetramethyl-1,3,2-dioxaborolan-2-yl)indolizine-7-carboxylate: in a 50 mL of dried three-necked flask, ethyl 5-acetyl-1-bromo-6-methylindolizine-7-carboxylate (2.0 g), Pd(dppf)Cl$_2$ (454 mg), bis(pinacolato)diboron (3.15 g) and potassium acetate (1.22 g) were added successively and dissolved in 1,4-dioxane (50 ml) and the mixture was stirred overnight at 110° C. After the reaction was completed, the reaction solution was extracted with ethyl acetate (100 mL×3), washed with water (30 mL×2) and saturated brine (30 mL). The organic phase was dried over anhydrous sodium sulfate, filtered and concentrated to obtain a crude product. The crude product was purified by column chromatography (petroleum ether: ethyl acetate=10:1, v/v) to give a yellow solid (910 mg, yield: 41%). MS (ESI) m/z 372 [M+H]$^+$.

Step 2: Preparation of ethyl 5-acetyl-6-methyl-1-(6-methylpyridazin-3-yl)indoizine-7-carboxylate: the operation procedures were the same as those in Step 3 of Example 1, yield 48%. MS (ESI) m/z 338 [M+H]$^+$.

Step 3: Preparation of isopropyl 6-methyl-1-(6-methylpyridazin-3-yl)-5-(1-(piperazin-1-yl)vinyl)indolizine-7-carboxylat e: the operation procedures were the same as those in Step 4 of Example 1. MS (ESI) m/z 420 [M+H]$^+$.

Step 4: Preparation of isopropyl 6-methyl-1-(6-methylpyridazin-3-yl)-5-(1-(4-(2,2,2-trifluoroethyl)piperazin-1-yl)vinyl)indolizine-7-carboxylate: triethylamine (272 mg), 2,2,2-trifluoroethyl trifluoromethanesulfonate (625 mg) were successively added to the crude product (600 mg) obtained in the previous step which was dissolved in 5 ml of anhydrous tetrahydrofuran, and the mixture was stirred overnight at room temperature, concentrated under reduced pressure, the crude product was separated by column chromatography to give a yellow solid (335 mg, yield in two steps 57%) MS (ESI) m/z 502 [M+H]$^+$.

Step 5: Preparation of 6-methyl-1-(6-methylpyridazin-3-yl)-5-(1-(4-(2,2,2-trifluoroethyl)piperazin-1-yl)vinyl)indolizine-7-carboxylic acid: the operations were the same as those in Step 5 of Example 1.

Step 6: Preparation of N-((4-methoxy-6-methyl-2-oxo-1,2-dihydropyridin-3-yl)methyl)-6-methyl-1-(6-methyl pyridazin-3-yl)-5-(1-(4-(2,2,2-trifluoroethyl)piperazin-1-yl)vinyl)indolizine-7-carboxamide: the operations were the same as those in Step 6 of Example 1, the yield in the two steps 70%. $^1$H NMR (400 MHz, DMSO-d$_6$) 11.44 (s, 1H), 8.48 (s, 1H), 8.09 (t, J=4.6 Hz, 1H), 7.93 (d, J=8.9 Hz, 1H),

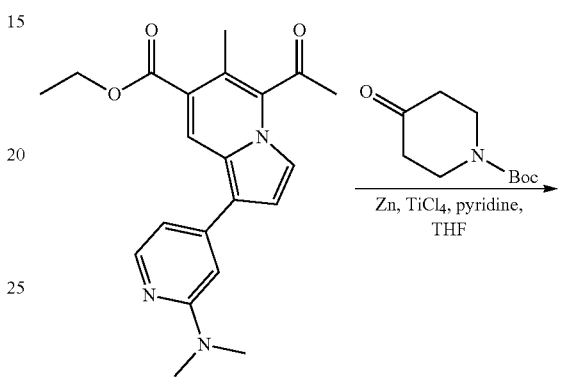

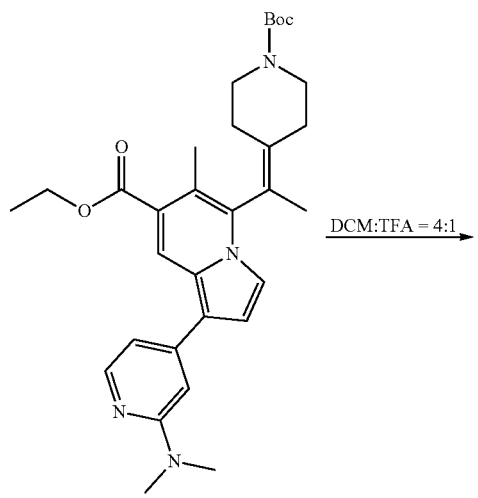

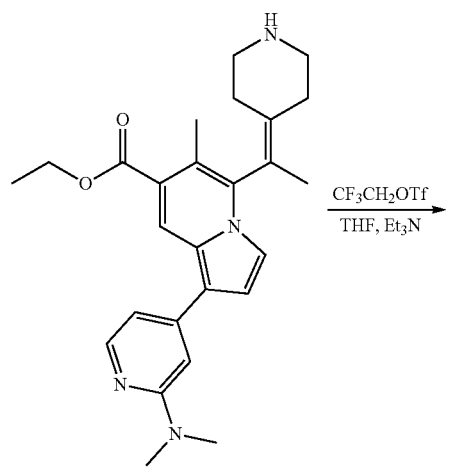

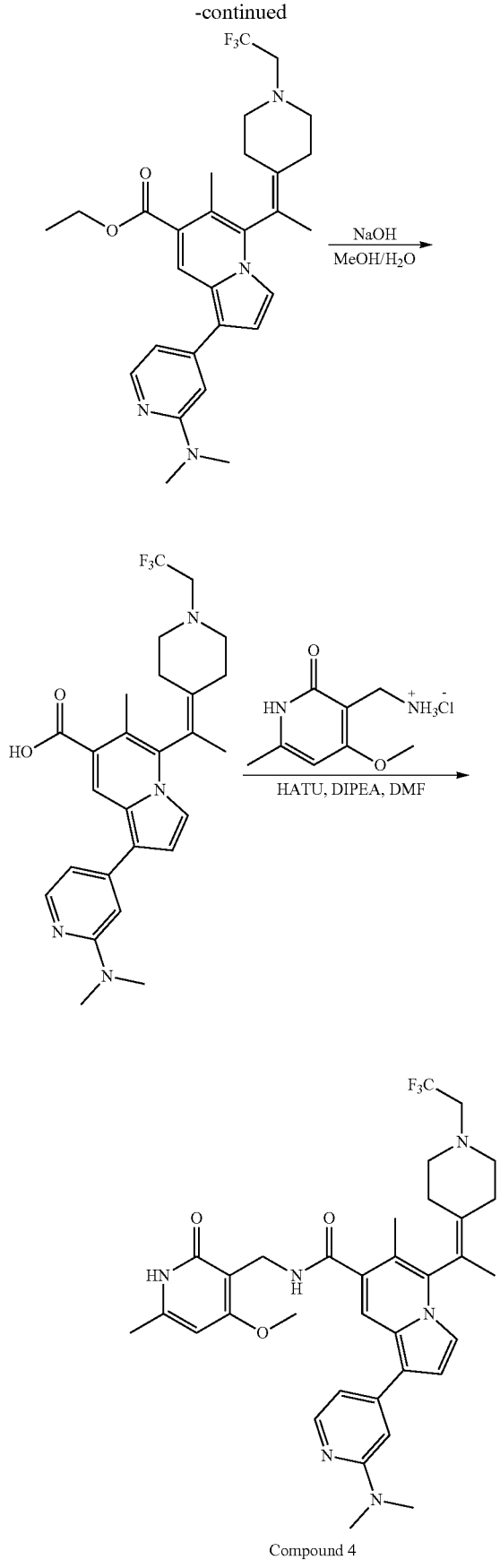

Compound 4

Step 1: Preparation of ethyl 5-(1-(1-(tert-butyloxycarbonyl)piperidin-4-alkenylene)ethyl)-1-(2-(dimethylamino)pyridin-4-yl)-6-methylindolizine-7-carboxylate: In a 100 ml round-bottom flask, 40 ml of dilute hydrochloric acid (content 1%) was added to 3.5 g of zinc powder, and the resultant was stirred at room temperature for 30 minutes, filtered by suction filtration, the solid thus obtained was washed successively with water, ether and ethanol, then the activated zinc powder was pumped with an oil pump to remove the residual solvent. Activated zinc powder (2.98 g) was added to a 250-mL three-necked flask replaced with nitrogen, and then the flask was transferred to an ice bath and added with 25 mL of anhydrous tetrahydrofuran, and then titanium tetrachloride (21 mL) was slowly added dropwise to the reaction solution. Thereafter, the reaction system was transferred to room temperature and stirred for 15 minutes, and then refluxed at 70° C. After 2 hours, the three-necked flask was transferred to room temperature for 15 minutes, and then it was transferred to an ice bath. Thereafter, a solution of 1-tert-butoxycarbonylpiperidone (2.05 g), ethyl 5-acetyl-1-(2-(dimethylamino)pyridin-4-yl)-6-methylindolizine-7-carboxylate (1.18 g) and pyridine (2.68 g) in tetrahydrofuran (50 ml) was slowly added dropwise to the three-necked flask. Thereafter, the solution was transferred to room temperature and stirred for 15 minutes, and then refluxed in an oil bath at 70° C. for 12 hours. The resultant was cooled to room temperature, quenched with saturated aqueous ammonium chloride solution, and added with water and ethyl acetate, let stand for 5 minutes. The upper organic phase was taken and concentrated under reduced pressure, and separated by column chromatography (ethyl acetate: petroleum ether=1:10 to 1:3, v/v) to give a yellow solid (185 mg, yield: 11%). $^1$H NMR (400 MHz, CDCl$_3$) 8.47 (s, 1H), 8.21 (d, J=5.3 Hz, 1H), 7.19 (d, J=2.7 Hz, 1H), 7.03 (d, J=2.8 Hz, 1H), 6.81 (dd, J=5.3, 1.3 Hz, 1H), 6.73 (s, 1H), 4.35 (q, J=7.1 Hz, 2H), 3.16 (s, 6H), 2.53 (s, 2H), 2.38 (s, 3H), 2.00 (s, 2H), 1.96 (s, 3H), 1.85 (d, J=13.1 Hz, 4H), 1.45 (s, 9H), 1.39 (t, J=7.1 Hz, 3H); MS (ESI) m/z 533 [M+H]$^+$.

Step 2: Preparation of ethyl 1-(2-(dimethylamino)pyridin-4-yl)-6-methyl-5-(1-(piperidin-4-alkenylene)ethyl)indoizine-7-carboxylate: In a 50 mL dried single-necked flask, compound ethyl 5-(1-(1-(tert-butyloxycarbonyl)piperidin-4-alkenylene)ethyl)-1-(2-(dimethylamino)pyridin-4-yl)-6-methylindolizine-7-carboxylate (92 mg), 2 ml of dichloromethane and 0.5 ml of trifluoroacetic acid were added thereto, the reaction solution was stirred at room temperature for 1 hour, and the reaction solution was neutralized with saturated sodium bicarbonate solution, extracted with dichloromethane (50 ml), and washed with water (50 ml×2) and saturated brine (50 ml), and the organic phase was concentrated to give a yellow liquid (29 mg, yield: 39%). MS (ESI) m/z 433 [M+H]$^+$.

Step 3: Preparation of ethyl 1-(2-(dimethylamino)pyridin-4-yl)-6-methyl-5-(1-(1-(2,2,2-trifluoroethyl)piperidin-4-alkenylene)ethyl)indolizine-7-carboxylate: the operation procedures were the same as those in Step 4 of Example 3. A yellow solid (33 mg, yield 96%) was obtained. MS (ESI) m/z 515 [M+H]$^+$.

Step 4: Preparation of 1-(2-(dimethylamino)pyridin-4-yl)-6-methyl-5-(1-(1-(2,2,2-trifluoroethyl)piperidin-4-alkenylene)ethyl)indolizine-7-carboxylic acid: the operation procedures were the same as those in Step 5 of Example 1. A yellow solid (21 mg, yield 70%) was obtained. MS (ESI) m/z 487 [M+H]$^+$.

Step 5: Preparation of 1-(2-(dimethylamino)pyridin-4-yl)-N-((4-methoxy-6-methyl-2-oxo-1,2-dihydropyridin-3-yl)methyl)-6-methyl-5-(1-(1-(2,2,2-trifluoroethyl)piperidin- 4-alkenylene)ethyl)indolizine-7-carboxamide: the operation procedures were the same as those in Step 6 of Example 1. A yellow solid (11 mg, yield 40%) was obtained. $^1$H NMR (400 MHz, CDCl$_3$) δ 11.91 (s, 1H), 8.07 (d, J=5.3 Hz, 1H), 7.80 (s, 1H), 7.73 (s, 1H), 7.12 (d, J=2.7 Hz, 1H), 6.96 (d, J=2.7 Hz, 1H), 6.75 (d, J=5.4 Hz, 1H), 6.62 (s, 1H), 5.85 (s, 1H), 4.57 (qd, J=14.7, 5.3 Hz, 2H), 3.87 (s, 3H), 3.07 (d, J=7.8 Hz, 6H), 2.98 (dd, J=19.1, 9.6 Hz, 2H), 2.85-2.77 (m, 2H), 2.56 (d, J=3.9 Hz, 2H), 2.25 (s, 3H), 2.16 (s, 3H), 2.01 (d, J=6.3 Hz, 4H), 1.92 (s, 3H); MS (ESI) m/z 637 [M+H]$^+$.

Example 5: Preparation of N-((4-methoxy-6-methyl-2-oxo-1,2-dihydropyridin-3-yl)methyl)-6-methyl-1-(2-(methylamino)pyridin-4-yl)-5-(1-(1-(2,2,2-trifluoroethyl)piperidin-4-alkenylene)ethyl)indolizine-7-carboxamide

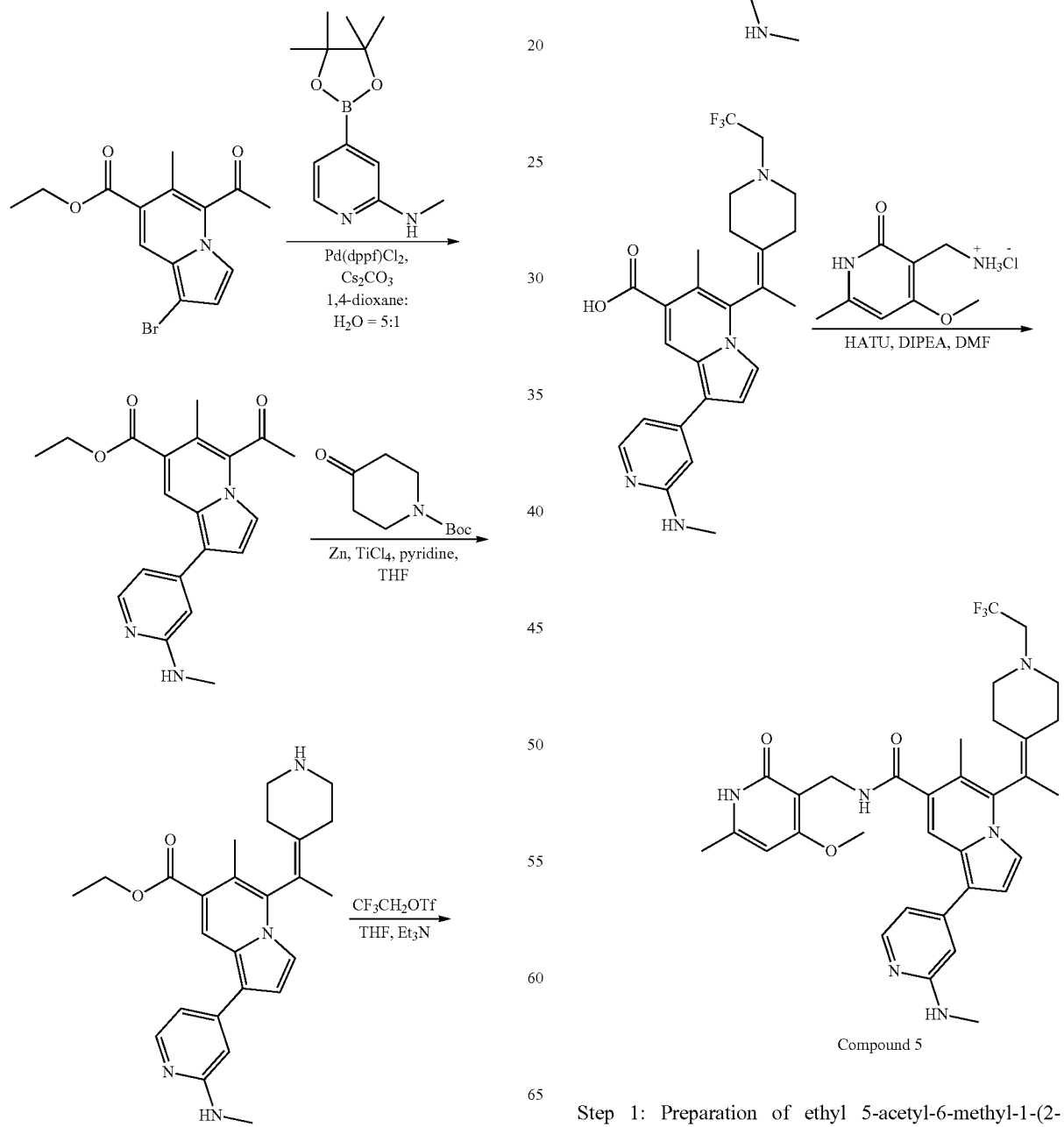

Compound 5

Step 1: Preparation of ethyl 5-acetyl-6-methyl-1-(2-(methylamino)pyridin-4-yl)indolizine-7-carboxylate: the operating procedures were the same as those in Step 3 of Example 1, yield 42%. MS (ESI) m/z 352 [M+H]+.

Step 2: Preparation of ethyl 6-methyl-1-(2-(methylamino) pyridin-4-yl)-5-(1-(piperidin-4-alkenylene)ethyl)indoizine-7-carboxylate: the operating procedures were the same as those in Step 1 of Example 4, yield 78%. MS (ESI) m/z 419 [M+H]+.

Step 3: Preparation of ethyl 6-methyl-1-(2-(methylamino) pyridin-4-yl)-5-(1-(1-(2,2,2-trifluoroethyl)piperidin-4-alkenylene)ethyl)indolizine-7-carboxylate: the operating procedures were the same as those in Step 4 of Example 3, yield 64%. MS (ESI) m/z 501 [M+H]+.

Step 4: Preparation of 6-methyl-1-(2-(methylamino)pyridin-4-yl)-5-(1-(1-(2,2,2-trifluoroethyl)piperidin-4-alkenylene)ethyl)indolizine-7-carboxylic acid: the operating procedures were the same as those in Step 5 of Example 1. MS (ESI) m/z 473 [M+H]+.

Step 5: Preparation of N-((4-methoxy-6-methyl-2-oxo-1,2-dihydropyridin-3-yl)methyl)-6-methyl-1-(2-(methylamino)pyridin-4-yl)-5-(1-(1-(2,2,2-trifluoroethyl)piperidin-4-alkenylene)ethyl)indoizine-7-carboxamide: the operating procedures were the same as those in Step 6 of Example 1. $^1$H NMR (400 MHz, CDCl$_3$) 12.26 (s, 1H), 7.94 (d, J=5.4 Hz, 1H), 7.82 (s, 1H), 7.12 (d, J=2.8 Hz, 1H), 6.96 (d, J=2.8 Hz, 1H), 6.80-6.74 (m, 1H), 6.57 (s, 1H), 5.86 (s, 1H), 4.57 (qd, J=14.7, 5.4 Hz, 2H), 3.87 (s, 3H), 2.97 (dd, J=19.1, 9.6 Hz, 2H), 2.86 (s, 3H), 2.84-2.76 (m, 2H), 2.56 (s, 2H), 2.26 (s, 3H), 2.18 (s, 3H), 2.01 (s, 2H), 1.91 (s, 3H), 1.86 (s, 2H); MS (ESI) m/z 623 [M+H]+.

Example 6: Biological Activity Assay

1. PRC2 Complex (Ezh2y641f) Activity Assay of the Compounds:

Test Method: Homogeneous Time-Resolved Fluorescence (HTRF)

Materials: PRC2 complex (EZH2 Y641F/EED/SUZ12/RbAp48/AEBP2) histone methyltransferase used in the test was purchased from Cisbio; substrate H3(1-50) K27me1 was a product of GL Biochem; methyl donor S-(5'-Adenosyl)-L-methionine chloride dihydrochloride (SAM) was purchased from Sigma-aldrich; Eu-labeled H3K27me3, Streptavidin-XL665 and the buffer used in the test were purchased from Cisbio.

Experiment method: PRC2 complex (EZH2 Y641F/EED/SUZ12/RbAp48/AEBP2), H3(1-50)me1 substrate, methyl donor SAM and the test compound were added to each well to reach a total of 10 µL reaction system and reacted in dark at room temperature for 4h. 5 µL of Eu-labeled H3K27 Me3 antibody and 5 µL of Streptavidin-XL665 were added to each well, mixed uniformly, and incubated at room temperature for 1 h. The fluorescence values at 620 nm and 665 nm were measured with a multi-label microplate analysis system (PerkinElmer Envision), and the HTRF signal ratio (665 nm/620 nm) was calculated for each well. The IC$_{50}$ values of the compounds were calculated using SoftMax Pro 5.4.1 software.

2. PRC2 Complex (EZH2 wild type) Activity Assay of the Compounds:

Test Method: Enzyme-linked immunosorbent assay (ELISA)

Materials: The PRC2 complex (EZH2/EED/SUZ12/RbAp48/AEBP2) histone methyltransferase used in the test was purchased from BPS; the substrate Biotin H3 (21-44) me0 was a product of AnaSpec; SAM, the product of GL Biochem, was purchased from Sigma; the methyl donor SAM was purchased from Sigma-aldrich; the H3K27me3 antibody was purchased from BPS.

Experiment method: a 96-well plate was coated with neutral avidin at a final concentration of 100 nM (100 µL/well), and the plate was placed in a wet box and shaken overnight, and then 100 µL of 3% BSA was added to each well for blocking at room temperature for 1 hour. In a blocked 96-well plate, a total volume of 100 µL of PRC2 complex (EZH2/EED/SUZ12/RbAp48/AEBP2), H3(21-44) me0 substrate, methyl donor SAM and the test compound was added to each well, and the plate was placed in a wet box and reacted on a shaker at room temperature for 1 h. The plate was washed with TBS-T [20 mM Tris-HCl (pH 7.2-7.4, room temperature), 150 mM NaCl, 0.1% (v/v) Tween-20] for 3 times, blocked with 3% BSA for 10 min, and added with anti-H3K27me3 antibody, and incubated in a wet box on a shaker at room temperature for 1 h. The plate was further washed with TBS-T for 3 times, and each well was blocked with 3% BSA for 10 minutes. Thereafter, horseradish peroxidase-labeled secondary antibody was added and reacted in a wet box on a shaker at room temperature for 1 h. Finally, the plate was further washed with TBS-T for 3 times, 2 mg/ml OPD chromogenic solution (100 µL/well) was added for color development, and the reaction was terminated with 2M H$_2$SO$_4$ (50 µL/well), the absorbance at 490 nm was read on a microplate reader, and the IC$_{50}$ values of the compounds were calculated using SoftMax Pro 5.4.1.

The results are shown in Table 1 below.

Table 1 shows the IC$_{50}$ values of some compounds

| Compd. | IC$_{50}$ (EZH2_Y641F, nM) | IC$_{50}$ (EZH2 Wild type, nM) | Compd. | IC$_{50}$ (EZH2_Y641F, nM) | IC$_{50}$ (EZH2 Wild type, nM) |
|---|---|---|---|---|---|
| 1 | 11.42 | / | 2 | 1.39 | / |
| 3 | 4.91 | / | 4 | 8.82 | / |
| 5 | 6.73 | / | | | |

Note:
"/" denotes not measured.

All documents mentioned in the present invention are cited as references in this application, just as each document is individually cited as a reference. In addition, it should be understood that, after reading the above contents of the present invention, those skilled in the art can make various changes or modifications to the present invention, and these equivalent forms also fall within the scope defined by the appended claims of the present application.

The invention claimed is:

1. An indolizine compound represented by formula I, a pharmaceutically acceptable salt, an enantiomer, or a diastereomer thereof,

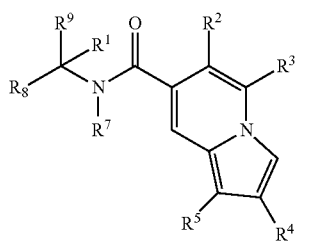

wherein, $R^1$ is selected from the group consisting of

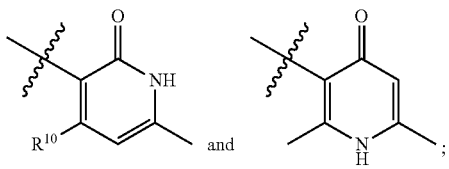

$R^{10}$ is selected from the group consisting of H, halogen, $-NH_2$, $-NO_2$, optionally substituted C1-C6 alkyl and optionally substituted C1-C4 alkoxy;

$R^2$ is selected from the group consisting of H, halogen, cyano and optionally substituted C1-C6 alkyl;

$R^3$ is

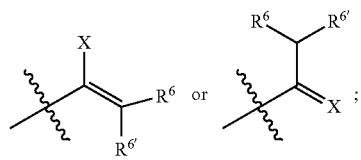

$R^6$ and $R^{6'}$ are each independently selected from the group consisting of H, methyl, ethyl, propyl and cyclopropyl, and at least one of $R^6$ and $R^{6'}$ is H;

X is an optionally substituted saturated or unsaturated 4-7 membered cyclic hydrocarbyl group or an optionally substituted 4-7 membered saturated or unsaturated heterocyclic group, and the heterocyclic group contains 1-2 heteroatoms selected from O, N, S and P;

$R^4$ and $R^5$ are independently selected from the group consisting of H, halogen, $-COOH$, $-CN$, optionally substituted C1-C6 alkyl, optionally substituted 6-16 membered aryl, optionally substituted 5-16 membered heteroaryl, optionally substituted 4-8 membered saturated or unsaturated cycloalkyl, optionally substituted 4-8 membered saturated or unsaturated heterocyclic group, optionally substituted C1-C6 alkylcarbonyl, optionally substituted $-C(O)O-(C1-C6$ alkyl), $-C(O)(NR^aR^b)$, dihydroxyboryl, optionally substituted C2-C8 alkenyl, optionally substituted C2-C8 alkynyl, optionally substituted C1-C6 alkyl sulfonyl group, optionally substituted C1-C6 alkyl sulfoxide group and optionally substituted C1-C6 alkyl mercapto group; wherein, the heteroaryl or heterocyclic group contains 1-3 heteroatoms selected from N, O, S, P; wherein, $R^a$ and $R^b$ are each independently selected from the group consisting of H, optionally substituted C1-C6 alkyl, optionally substituted 3-8 membered cycloalkyl, and optionally substituted 4-8 membered heterocyclic group, or $R^a$ and $R^b$ are connected together with N to form an optionally substituted 4-8 membered heterocyclic ring; wherein the heterocyclic ring contains 1-3 heteroatoms selected from N, O, S and P;

$R^7$ is selected from the group consisting of H and optionally substituted C1-C6 alkyl;

$R^8$ and $R^9$ are each independently selected from the group consisting of hydrogen, deuterium and optionally substituted C1-C6 alkyl;

the optionally substituted substituents in $R^2$, $R^7$, $R^8$, $R^9$, $R^{10}$, $R^a$ and $R^b$ include one or more substituents selected from the group consisting of H, halogen, C1-C4 alkyl, C1-C4 haloalkyl, nitro, $-OH$, amino, methoxy and dimethylamino.

2. The indolizine compound represented by formula I of claim 1, the pharmaceutically acceptable salt, enantiomer, or diastereomer thereof, wherein, $R^1$ is

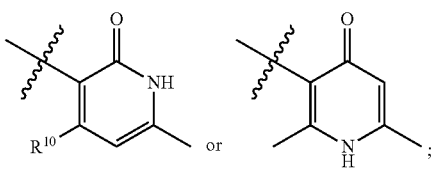

$R^{10}$ is selected from the group consisting of H, halogen, $-NH_2$, $-NO_2$, optionally substituted C1-C6 alkyl and optionally substituted C1-C4 alkoxy;

$R^2$ is selected from the group consisting of H, halogen, cyano and optionally substituted C1-C6 alkyl; $R^2$ is optionally substituted C1-C4 alkyl; further $R^2$ is methyl;

$R^3$ is

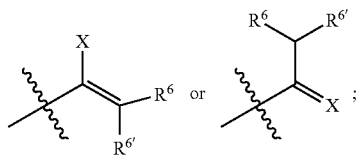

$R^6$ and $R^{6'}$ are each independently selected from the group consisting of H, methyl, ethyl, propyl and cyclopropyl, and at least one of $R^6$ and $R^{6'}$ is H;

X is selected from the group consisting of an optionally substituted saturated or unsaturated 4-7 membered cyclic hydrocarbyl group, and an optionally substituted 4-7 membered saturated or unsaturated heterocyclic group; wherein, the heterocyclic group contains 1-2 heteroatoms selected from O, N, S, P; the substituent in X is selected from the group consisting of —OH, halogen, tert-butyloxycarbonyl, —NR$^s$R$^t$, C1-C4 alkyl substituted with 1-3 R$^x$s, C1-C4 alkoxy substituted with 1-3 R$^x$s, C1-C4 alkylcarbonyl substituted with 1-3 R$^x$s, C1-C4 alkoxycarbonyl substituted with 1-3 R$^x$s and C1-C4 alkylsulfonyl substituted with 1-3 R$^x$s; each R$^x$ is independently selected from the group consisting of H, halogen, methylamino, dimethylamino, amino, —OH, methoxy and ethoxy;

R$^s$ and R$^t$ are each independently selected from the group consisting of: H, C1-C4 alkyl, C1-C4 haloalkyl,

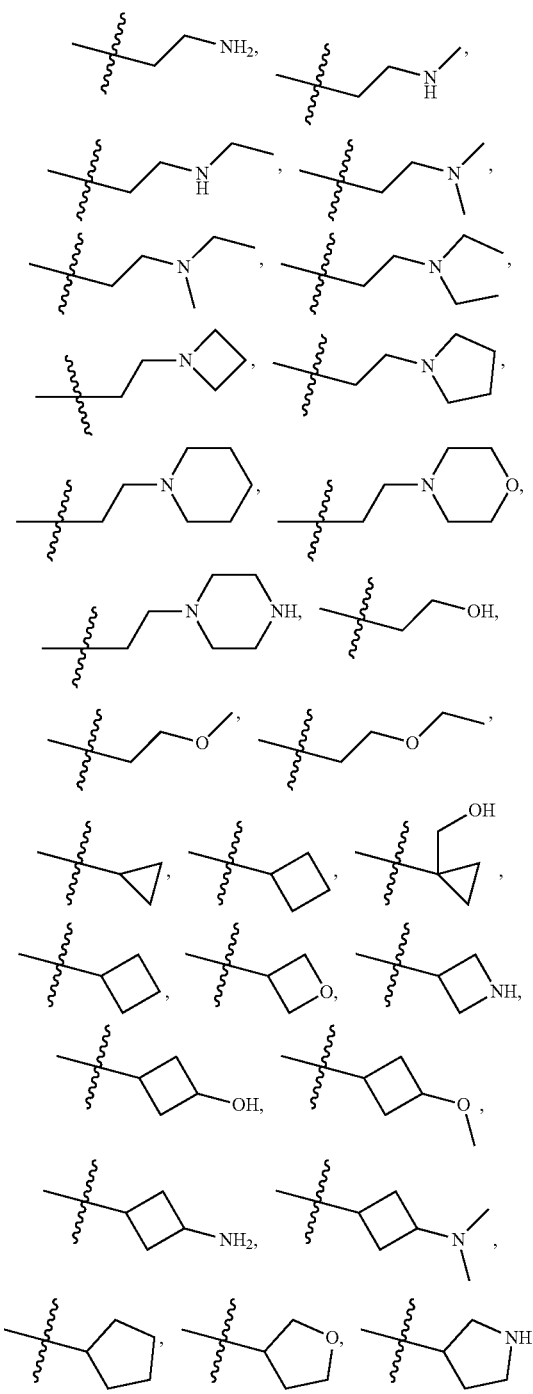

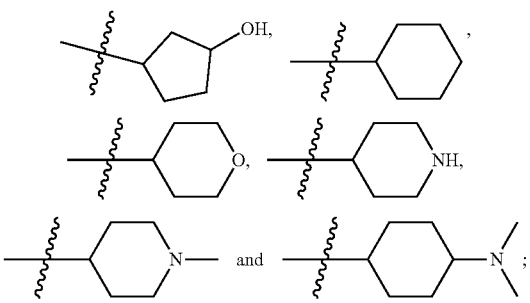

R$^4$ and R$^5$ are each independently selected from the group consisting of H, halogen, —COOH, —CN, optionally substituted C1-C6 alkyl, optionally substituted 6-16 membered aryl, optionally substituted 5-16 membered heteroaryl, optionally substituted 4-8 membered saturated or unsaturated cycloalkyl, optionally substituted 4-8 membered saturated or unsaturated heterocyclic group, optionally substituted C1-C6 alkylcarbonyl, optionally substituted —C(O)O—(C1-C6 alkyl), —C(O)(NR$^a$R$^b$), dihydroxyboryl, optionally substituted C2-C8 alkenyl, optionally substituted C2-C8 alkynyl, optionally substituted C1-C6 alkyl sulfonyl group, optionally substituted C1-C6 alkyl sulfoxide group and optionally substituted C1-C6 alkyl mercapto group; the heteroaryl or heterocyclic group contains 1-3 heteroatoms selected from N, O, S, P; and the substituents in R$^4$ and R$^5$ are selected from the group consisting of halogen, —CN, R$^{45}$ (C1-C4 alkyl), R$^{45}$ (C1-C4 alkoxy), R$^{45}$ (C1-C4 alkyl) acyl, R$^{45}$ (C1-C4 alkyl) sulfonyl, R$^{45}$ (C3-C8 cycloalkyl), R$^{45}$ (4-8 membered heterocyclic group) and —NR$^c$R$^d$; the heterocyclic group is a heterocyclic group containing 1-2 heteroatoms selected from N and O;

each R$^{45}$ is independently selected from the group consisting of H, —OH, halogen, tert-butyloxycarbonyl, halogenated C1-C4 alkyl, C1-C4 alkyl, C1-C4 alkoxy, C1-C4 acyl, dimethylamino, methylamino, diethylamino, methylethylamino, ethylamino,

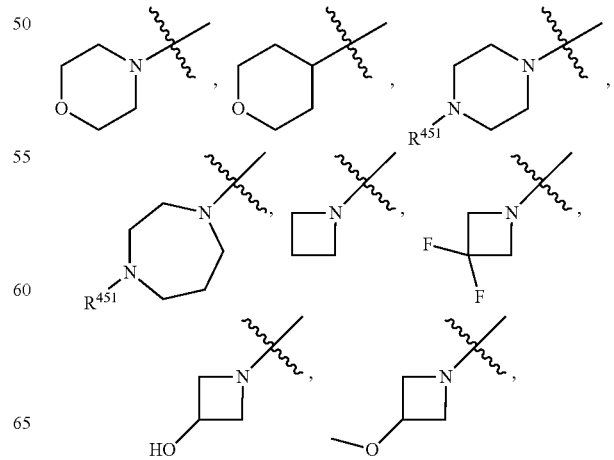

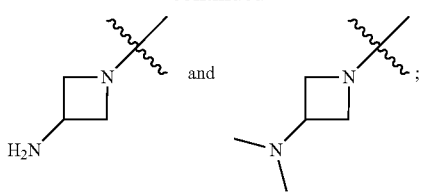

and $R^{451}$ is selected from the group consisting of H, C1-C4 alkyl; wherein, $R^a$ and $R^b$ are each independently selected from the group consisting of H, optionally substituted C1-C6 alkyl, optionally substituted 3-8 membered cycloalkyl and optionally substituted 4-8 membered heterocyclic group, or Ra and Rb are connected together with N to form optionally substituted 4-8 membered heterocyclic ring;

wherein the heterocyclic ring contains 1-3 heteroatoms selected from N, O, S and P;

$R^c$ and $R^d$ are each independently selected from the group consisting of: H, C1-C4 alkyl, C1-C4 haloalkyl,

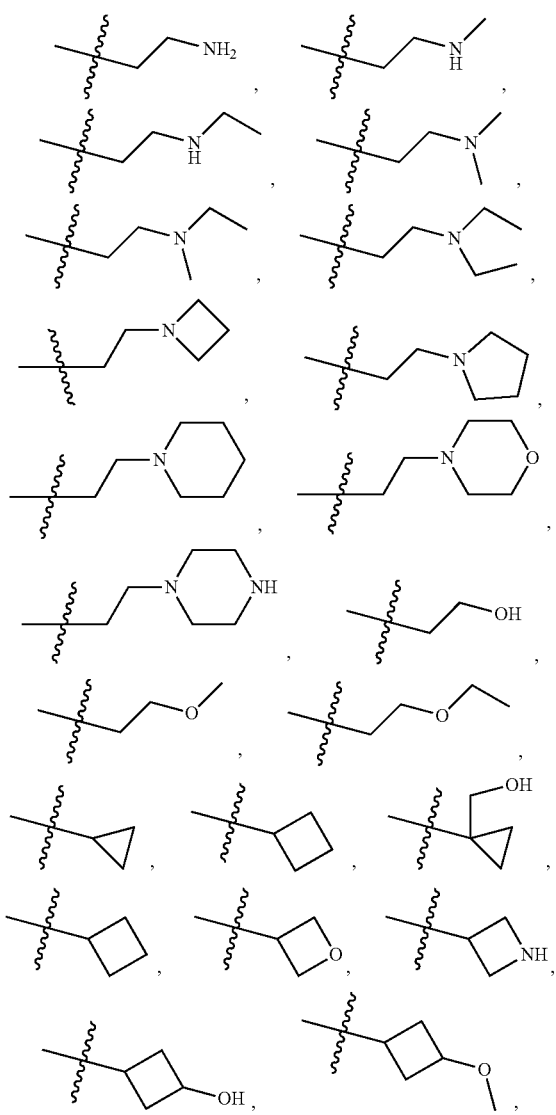

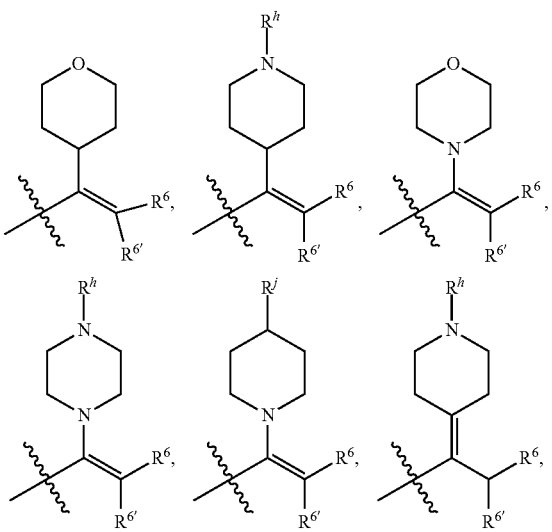

$R^7$ is selected from the group consisting of H and optionally substituted C1-C6 alkyl;

$R^8$ and $R^9$ are each independently selected from the group consisting of hydrogen, deuterium and optionally substituted C1-C6 alkyl;

the substituents in $R^2$, $R^7$, $R^8$, $R^9$, $R^{10}$, $R^a$, and $R^b$ include one or more substituents selected from the group consisting of H, halogen, C1-C4 alkyl, C1-C4 haloalkyl, nitro, —OH, amino, methoxy and dimethylamino.

3. The indolizine compound represented by formula I of claim 1, the pharmaceutically acceptable salt, enantiomer, or diastereomer thereof, wherein, $R^3$ is selected from the group consisting of:

-continued

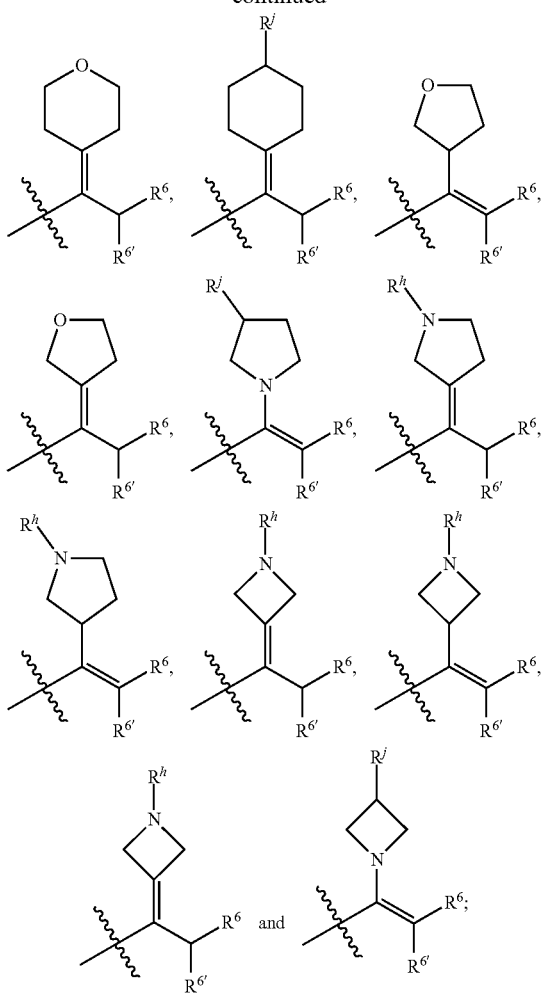

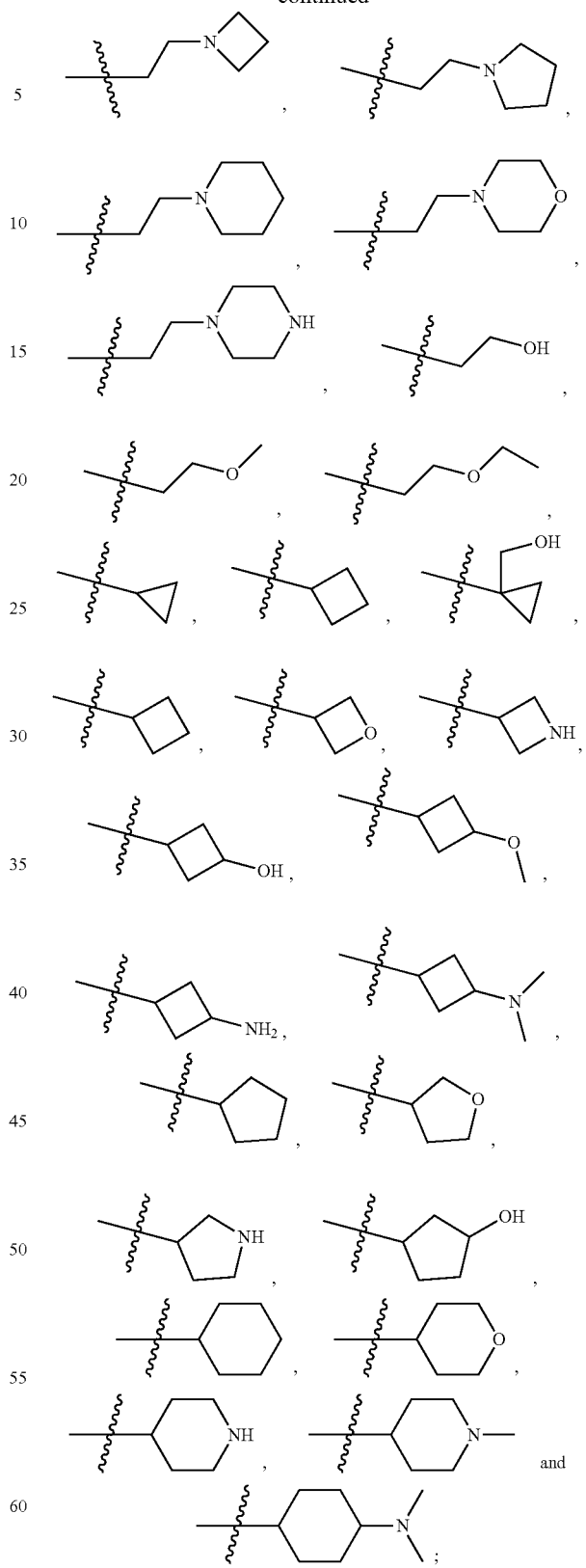

where $R^h$ is selected from the group consisting of H, C1-C4 alkyl substituted with 1-3 $R^x$s, C1-C4 alkylcarbonyl substituted with 1-3 $R^x$s, C1-C4 alkoxycarbonyl substituted with 1-3 $R^x$s, C1-C4 alkylsulfonyl substituted with 1-3 $R^x$s and tert-butyloxycarbonyl;

$R^j$ is selected from the group consisting of —OH, halogen, C1-C4 alkyl substituted with 1-3 $R^x$s, C1-C4 alkoxy substituted with 1-3 $R^x$s, and —$NR^sR^t$;

$R^x$ is selected from the group consisting of H, halogen and —OH;

$R^s$ and $R^t$ are each independently selected from the group consisting of H, C1-C4 alkyl, C1-C4 haloalkyl,

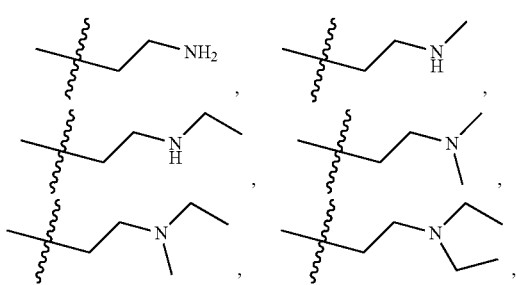

$R^6$ and $R^{6'}$ are each independently selected from the group consisting of H, methyl and ethyl, and at least one of $R^6$ and $R^{6'}$ is H;

$R^3$ is selected from the group consisting of:

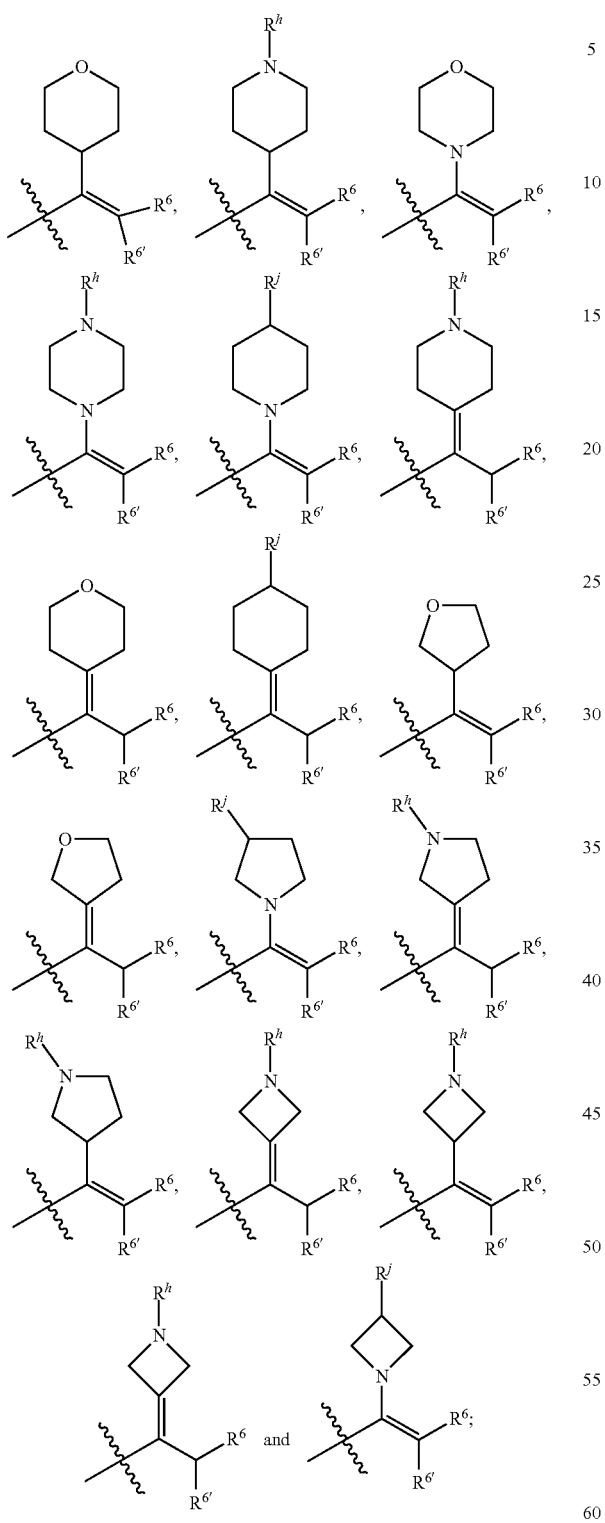

where $R^h$ is selected from the group consisting of H and $R^x$ (C1-C3 alkyl);

$R^j$ is selected from the group consisting of —OH, halogen, $R^x$ (C1-C3 alkyl), $R^x$ (C1-C3 alkoxy) and —N(C1-C3 alkyl)$_2$;

$R^x$ is selected from the group consisting of H, halogen, trifluoromethyl and difluoromethyl;

$R^6$ and $R^{6'}$ are each independently selected from the group consisting of H, methyl and ethyl, and at least one of $R^6$ and $R^{6'}$ is H;

$R^3$ is selected from the group consisting of:

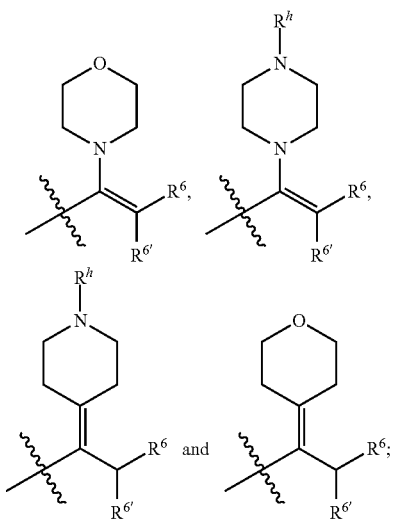

$R^h$ is selected from C1-C3 alkyl substituted with fluorine;
$R^6$ and $R^{6'}$ are each independently selected from H and methyl, and at least one of $R^6$ and $R^{6'}$ is H.

4. The indolizine compound represented by formula I of claim 1, the pharmaceutically acceptable salt, enantiomer, or diastereomer thereof, wherein, $R^4$ or $R^5$ are each independently selected from the group consisting of: H, $R^{55}$C1-C4 alkyl, —CN, halogen, $R^{55}$C1-C4 alkylcarbonyl, $R^{55}$ (C1-C4 alkoxy) carbonyl, —COOH, —C(O)(NR$^a$R$^b$),

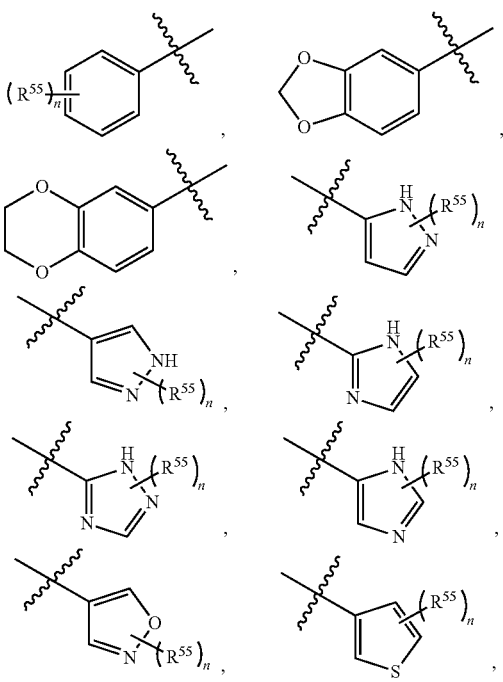

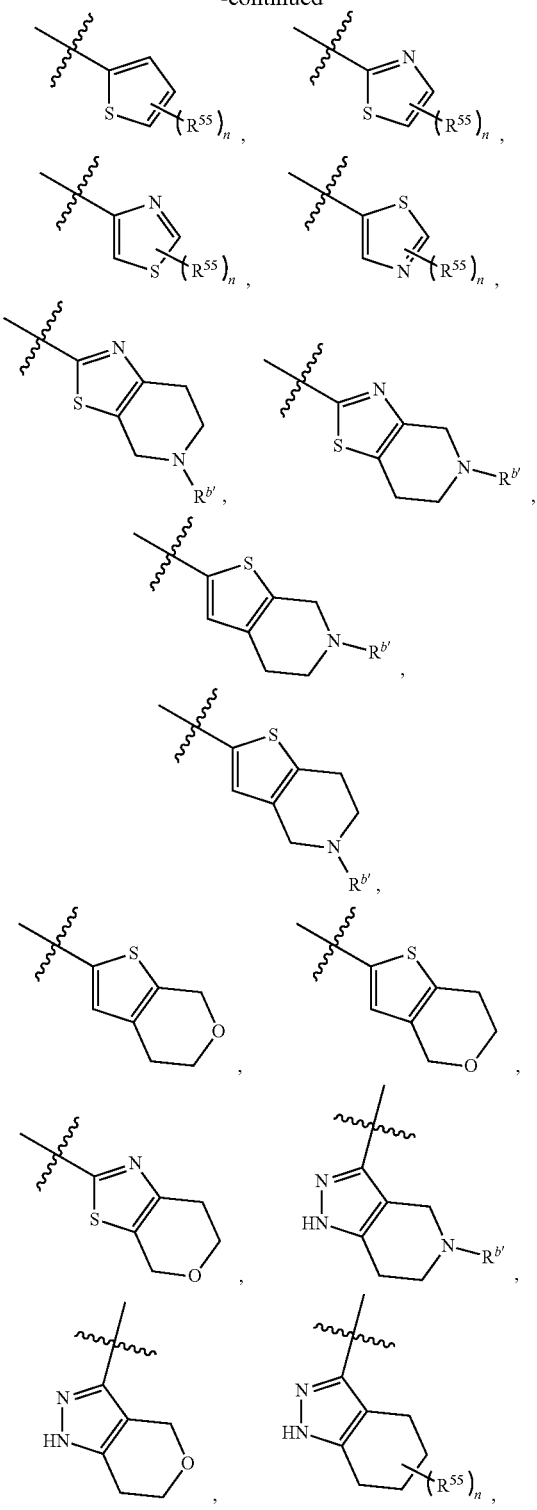
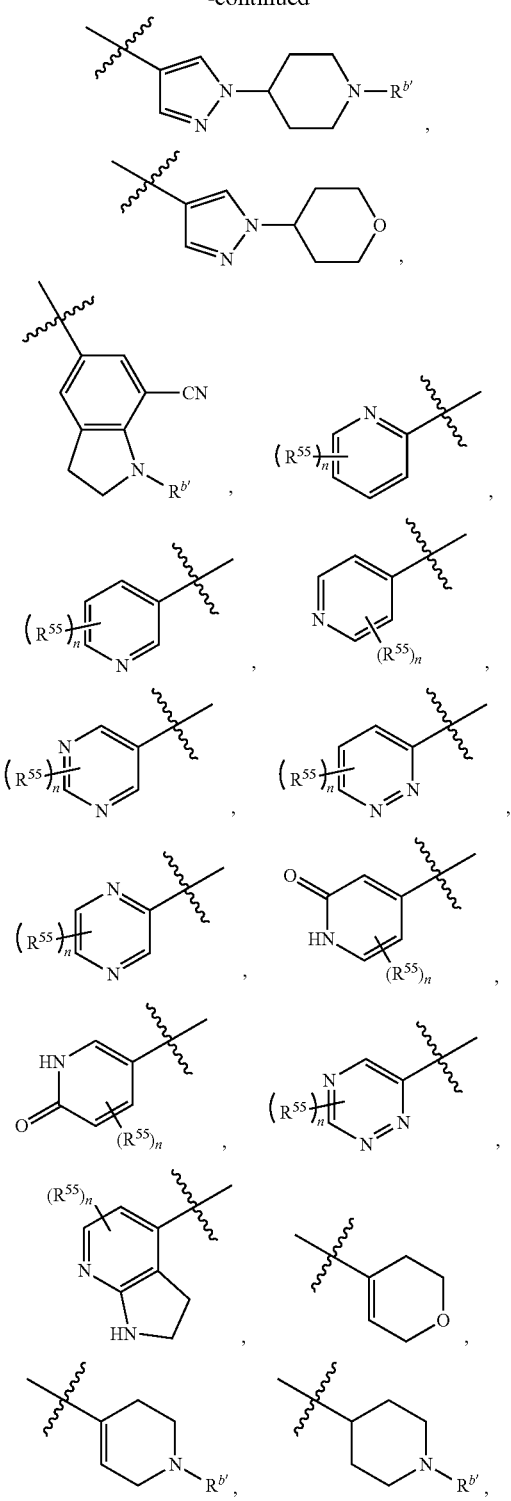
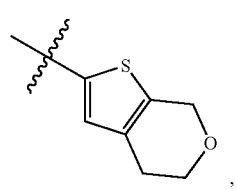
and R[55]C1-C3 alkynyl;
n is the number of R[55] substituents, and is selected from 1, 2 and 3;
R[55] is selected from the group consisting of H, R[551]C1-C4 alkyl, R[551]C3-C8 cycloalkyl, halogen, —CN, —NR-$^c$R$^d$, (R[551]C1-C4 alkyl)O—, R[551]C1-C4 alkyl sulfonyl group,

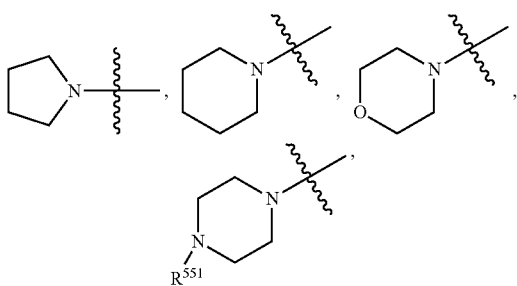

R$^{551}$ (C1-C6 alkyl)OC(O)—, —COOH and —C(O)(NR$^a$R$^b$); wherein R$^{551}$ is H, —OH, halogen, halogenated C1-C4 alkyl, C1-C4 alkyl, C1-C4 alkoxy, amino, dimethylamino, methylamino, diethylamino, methylethylamino, ethylamino,

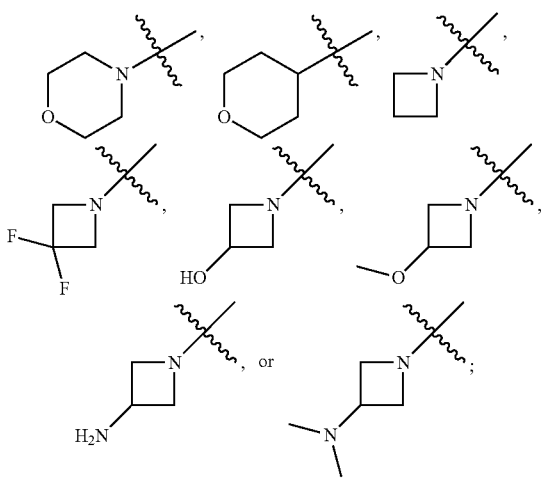

R$^a$ and R$^b$ are each independently selected from the group consisting of H, C1-C4 alkyl, Rb"(C1-C4)alkyl, phenyl, halophenyl, and R$^{b'}$ substituted heterocyclic group; or R$^a$ and R$^b$ are connected together with N to form a 4-8 membered heterocyclic group substituted with R$^{b'}$, the heterocyclic group contains 1-2 heteroatoms selected from N and O;

R$^{b''}$ is selected from the group consisting of H, —OH, C1-C3 alkoxy, dimethylamino,

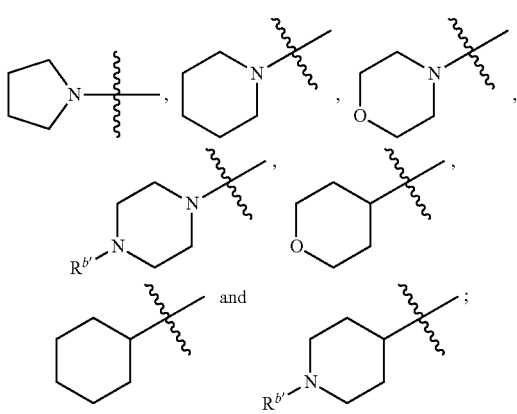

R$^{b'}$ is selected from the group consisting of H, C1-C4 alkyl, tert-butyloxycarbonyl and C1-C4 acyl;

R$^4$ or R$^5$ are each independently selected from the group consisting of H,

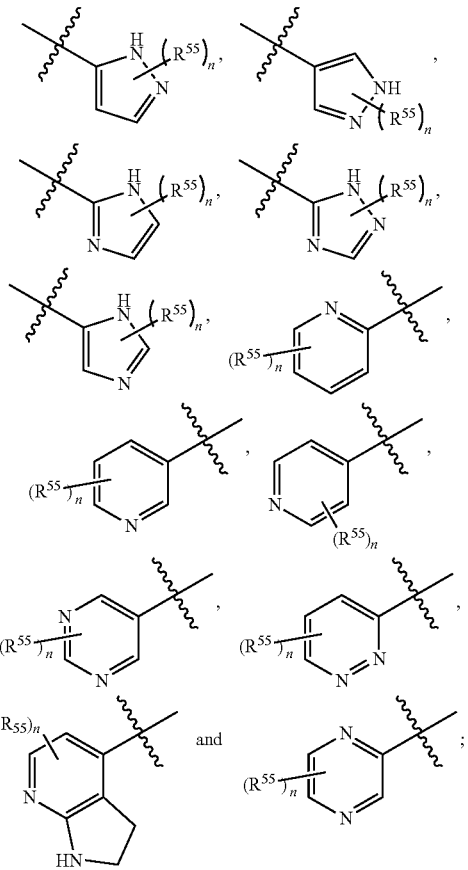

n is the number of R$^{55}$ substituents, and is selected from 1 and 2;

R$^{55}$ is selected from the group consisting of H, C1-C4 alkyl, halogen, —NH$_2$, (C1-C2 alkyl)NH— and dimethylamino.

5. The indolizine compound represented by formula I of claim 1, the pharmaceutically acceptable salt, enantiomer, or diastereomer thereof, wherein, R$^3$ is

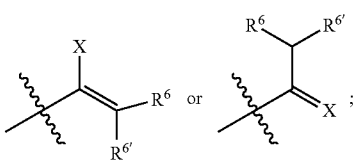

R$^6$ and R$^{6'}$ are each independently selected from the group consisting of H, methyl, ethyl and propyl, and at least one of R$^6$ and R$^{6'}$ is H;

X is selected from the group consisting of optionally substituted pyranyl, optionally substituted piperidinyl, optionally substituted piperazinyl and optionally substituted morpholinyl, and the substituent in X is selected from the group consisting of C1-C4 alkyl and halogenated C1-C4 alkyl;

the substituent in X is trifluoroethyl;
R² is methyl;
R¹⁰ is selected from the group consisting of unsubstituted or halogenated C1-C4 alkyl and unsubstituted or halogenated C1-C4 alkoxy;
R⁴, R⁵ are each independently selected from the group consisting of H, optionally substituted pyridyl, optionally substituted pyrimidinyl, optionally substituted pyridazinyl, optionally substituted pyrazolyl, optionally substituted triazolyl and optionally substituted pyrrolopyridyl;
the substituents in R⁴ and R⁵ are selected from the group consisting of H, C1-C4 alkyl, halogen and —NR$^c$R$^d$;
R$^c$ and R$^d$ are each independently selected from the group consisting of H, C1-C4 alkyl and halogenated C1-C4 alkyl.

6. The indolizine compound represented by formula I of claim 1, the pharmaceutically acceptable salt, enantiomer, or diastereomer thereof, wherein,
R² is methyl;
R³ is

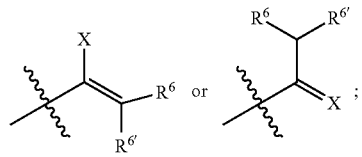

R⁶ and R⁶' are each independently selected from H and methyl, and at least one of R⁶ and R⁶' is H;
X is selected from the group consisting of morpholinyl, trifluoroethylpiperazinyl and trifluoroethylpiperidinyl; further morpholinyl, 2,2,2-trifluoroethylpiperazinyl or 2,2,2-trifluoroethyl piperidinyl;
R⁴ and R⁵ are each independently selected from the group consisting of H, dimethylaminopyridine and methylaminopyridine; further H, 2-dimethylaminopyridine or 2-methylaminopyridine;
R⁷, R⁸ and R⁹ are hydrogen;
R¹⁰ is methoxy.

7. The indolizine compound represented by formula I of claim 1, the pharmaceutically acceptable salt, enantiomer, or diastereomer thereof, wherein the indolizine compound represented by Formula I is selected from the following compounds:

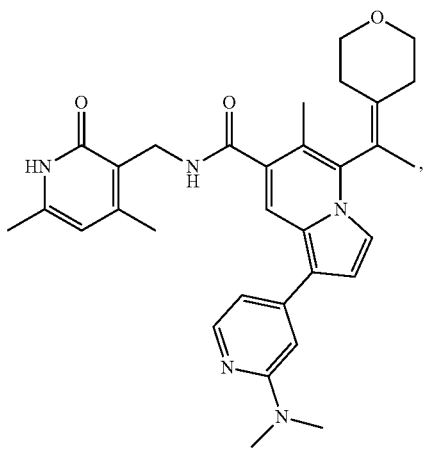

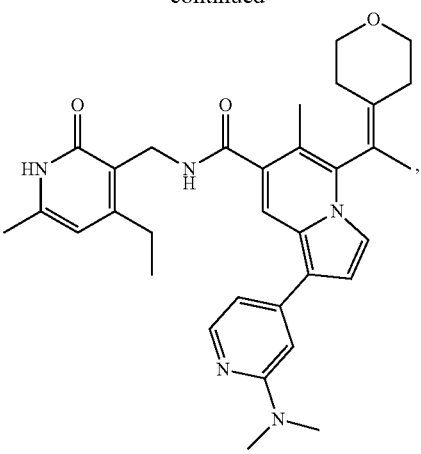

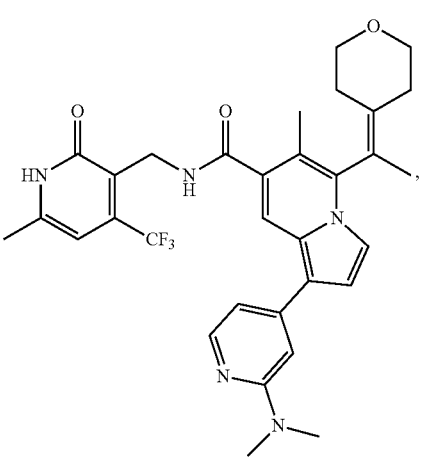

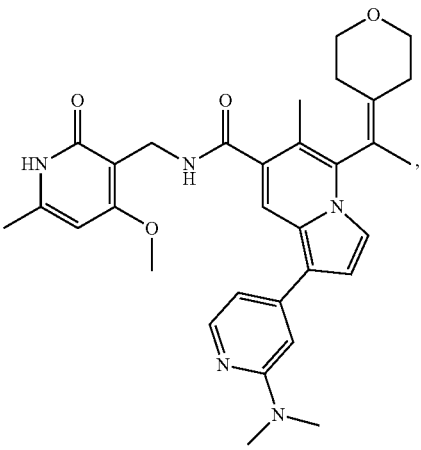

-continued
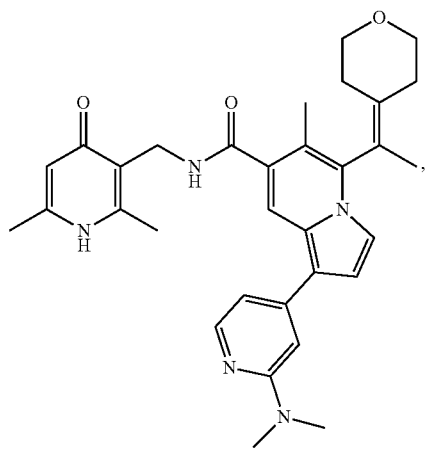
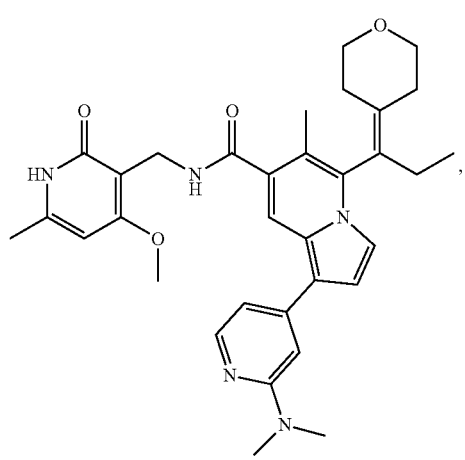
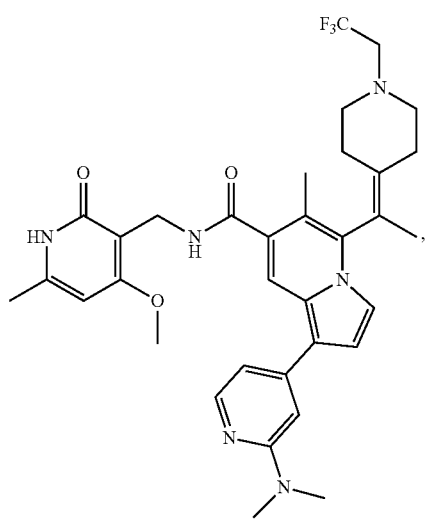
-continued
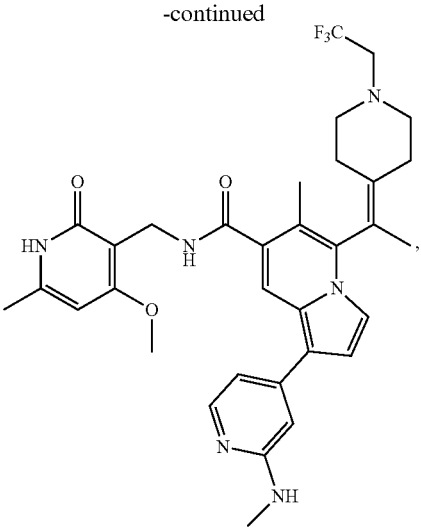
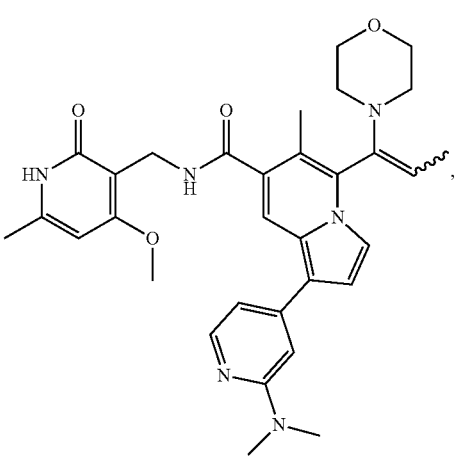
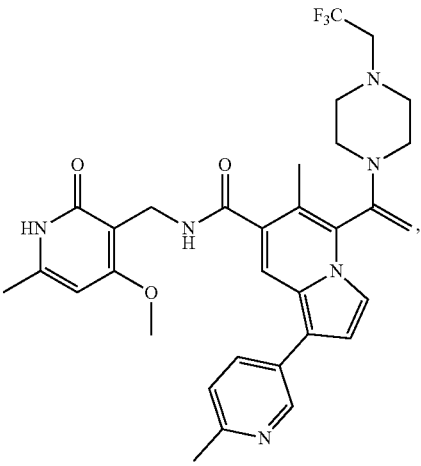

69
-continued
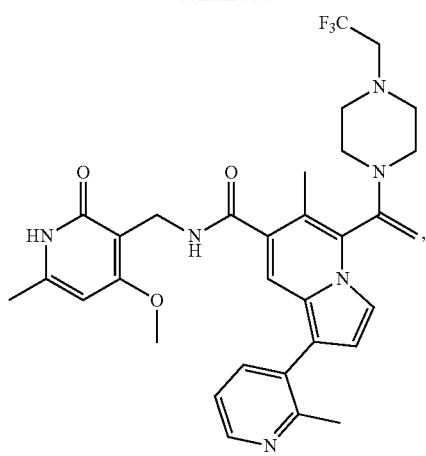
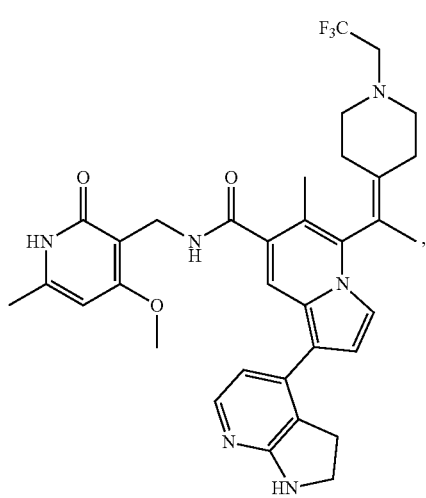
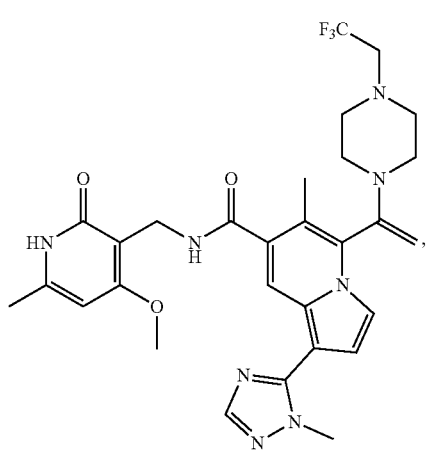
70
-continued
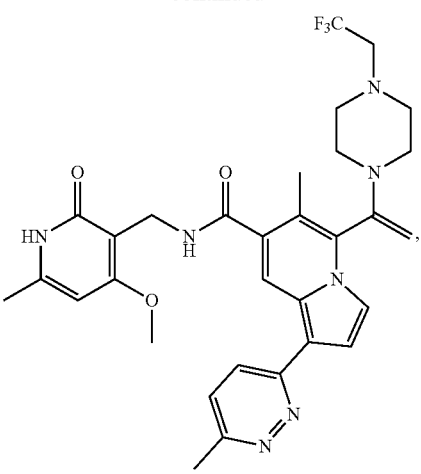
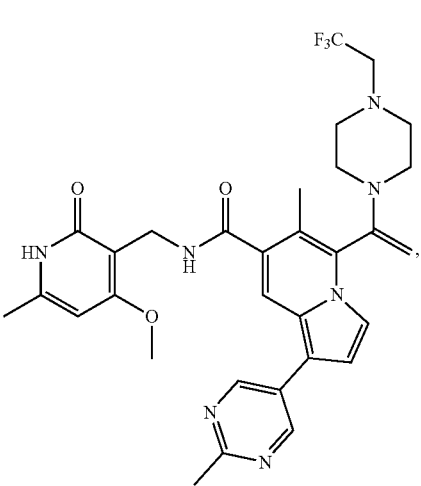
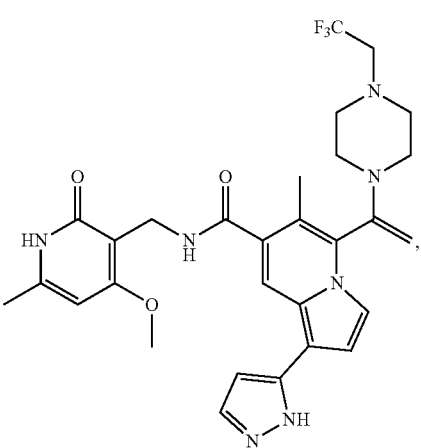

71
-continued

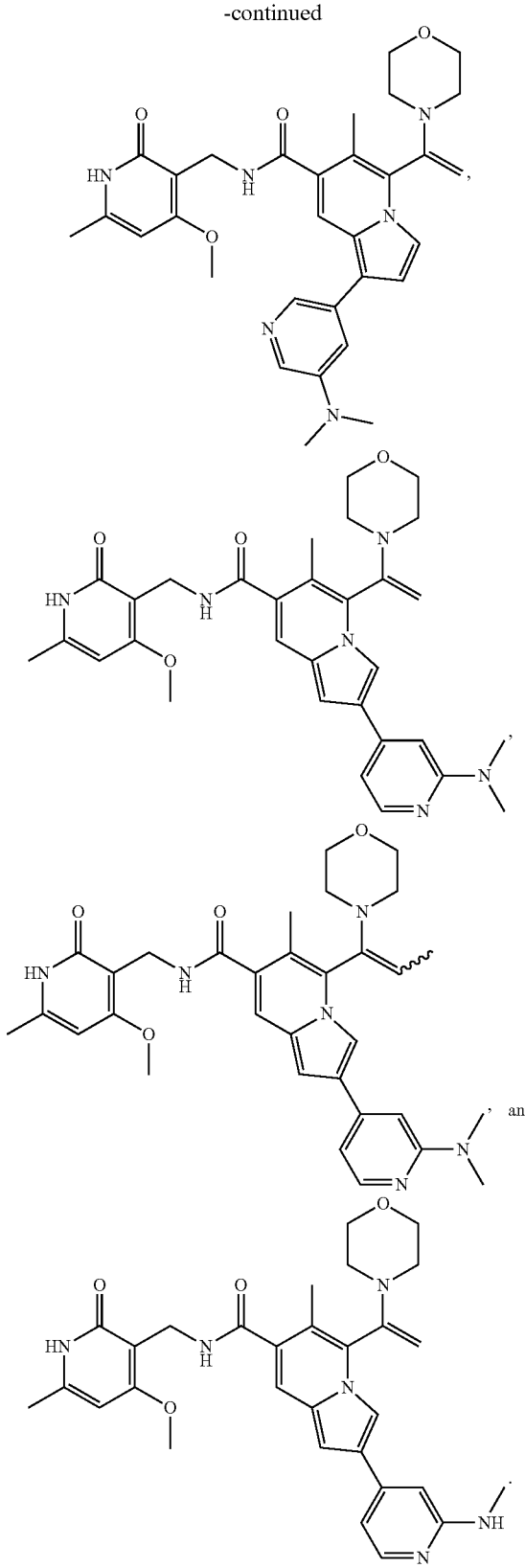

8. A method for preparing the indolizine compound represented by Formula I of claim 1 or the pharmaceutically acceptable salt thereof, the method comprising one of the following methods:

72

Method I

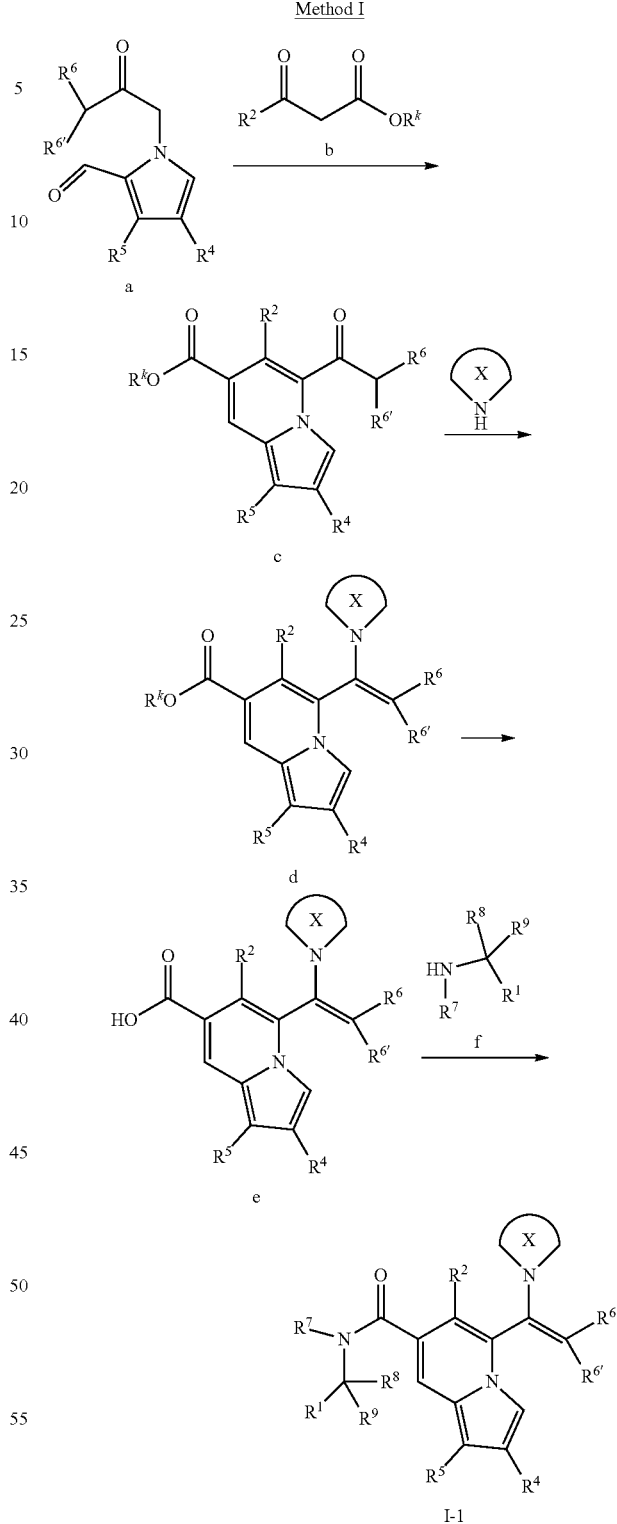

(1) in the presence of a base, compound a is reacted with compound b via a condensation reaction to produce compound c;

(2) in the presence of a Lewis acid, compound c is reacted with secondary amine via dehydration reaction to produce enamine compound d;

(3) compound d is hydrolyzed to produce compound e;
(4) compound e is reacted with amine f via condensation reaction to produce compound I-1,
wherein, $R^1$, $R^2$, $R^4$, $R^5$, $R^6$, $R^{6'}$, $R^7$, $R^8$ and $R^9$ are as defined in claim 1, and $R^k$ is a C1-C4 linear or branched alkyl group; circle X is an optionally substituted 4-7 membered saturated or unsaturated heterocyclic group, and the heterocyclic group contains at least one N atom, and the optional substituent thereof is defined as the substituent in X as defined in claim 1;

Method II

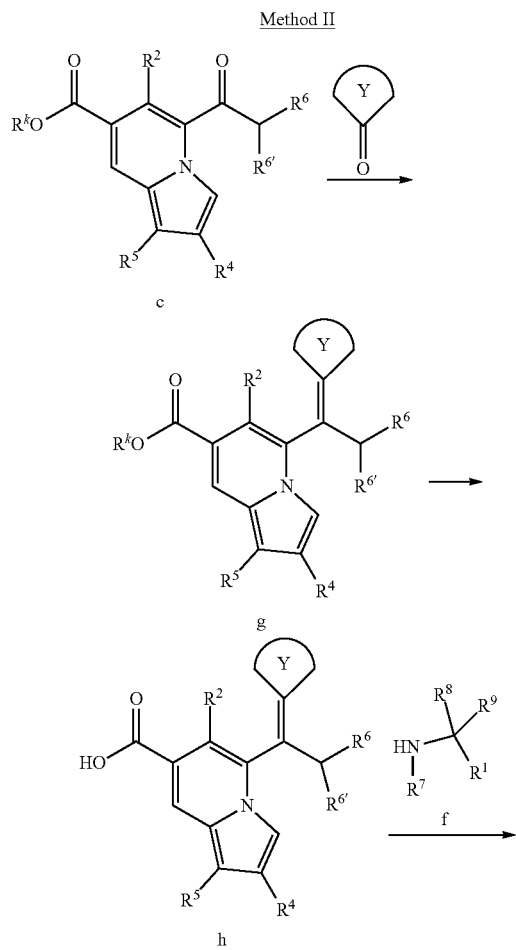

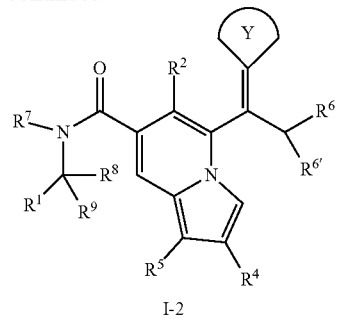

I-2

(5) in the presence of titanium trichloride or titanium tetrachloride and a reducing agent, compound c is reacted with a corresponding ketone in an inert solvent via McMurry reaction to produce compound g;

(6) compound g undergoes a hydrolysis reaction to produce compound h;

(7) compound g is reacted with amine f via condensation reaction to produce compound 1-2;

wherein, $R^1$, $R^2$, $R^4$, $R^5$, $R^6$, $R^{6'}$, $R^7$, $R^8$ and $R^9$ are as defined in claim 1, and $R^k$ is a C1-C4 linear or branched alkyl group; circle Y is an optionally substituted saturated or unsaturated 4-7 membered cyclic hydrocarbyl group or optionally substituted 4-7 membered saturated or unsaturated heterocyclic group, and the heterocyclic group contains 1-2 heteroatoms selected from O, N, S and P, and the optional substituent thereof is defined as the substituent in X as defined in claim 1.

9. A pharmaceutical composition, comprising:

an active component in a therapeutically effective amount, the active component is selected from the indolizine compound represented by formula I of claim 1, the pharmaceutically acceptable salt, enantiomer, or diastereomer thereof; and a pharmaceutically acceptable carrier.

* * * * *